US012729180B2

(12) United States Patent
Mhaske et al.

(10) Patent No.: US 12,729,180 B2
(45) Date of Patent: Sep. 8, 2026

(54) FUNCTIONALIZED MALEIMIDES AND ISOMALEIMIDES AND A PROCESS FOR PREPARATION THEREOF

(71) Applicant: COUNCIL OF SCIENTIFIC AND INDUSTRIAL RESEARCH, New Delhi (IN)

(72) Inventors: Santosh Baburao Mhaske, Pune (IN); Amol Basagonda Viveki, Pune (IN); Mahesh Dattatraya Pol, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 437 days.

(21) Appl. No.: 18/568,726

(22) PCT Filed: Jun. 9, 2022

(86) PCT No.: PCT/IN2022/050535
§ 371 (c)(1),
(2) Date: Dec. 8, 2023

(87) PCT Pub. No.: WO2022/259266
PCT Pub. Date: Dec. 15, 2022

(65) Prior Publication Data

US 2024/0294473 A1 Sep. 5, 2024

(30) Foreign Application Priority Data

Jun. 9, 2021 (IN) ............................ 202111016679

(51) Int. Cl.

| | |
|---|---|
| ***C07D 207/444*** | (2006.01) |
| ***A61K 31/341*** | (2006.01) |
| ***A61K 31/4015*** | (2006.01) |
| ***C07D 207/44*** | (2006.01) |
| ***C07D 307/66*** | (2006.01) |

(52) U.S. Cl.
CPC ........ *C07D 207/444* (2013.01); *A61K 31/341* (2013.01); *A61K 31/4015* (2013.01); *C07D 207/44* (2013.01); *C07D 307/66* (2013.01)

(58) Field of Classification Search
CPC .............. C07D 207/44; C07D 207/444; C07D 3087/66; A61K 31/341; A61K 31/4015
See application file for complete search history.

(56) References Cited

PUBLICATIONS

Kaeobamrung, et al., Chiral N-heterocyclic carbene-catalyzed generation of ester enolate equivalents from unsaturated aldehydes for enantioselective Diels-Alder reactions, Proceedings of the National Academy of Sciences, 107(48), pp. 20661-20665 (2010) (Year: 2010).*
Guo et al; "N-Heterocyclic Carbene Catalyzed Formal [3+2] Annulation Reaction of Enals: An Efficient Enantioselective Access to Spiro-Heterocycles"; Angew. Chem. Int. Ed. 2014, 53, 1-6.
International Search Report and Written Opinion dated Jul. 29, 2022 issued in PCT/IN2022/050535.
Kaeobamrung et al.; "Chiral N-heterocyclic carbene-catalyzed generation of ester enolate equivalents from,—unsaturated aldehydes for enantioselective Diels-Alder reactions"; PNAS, Nov. 30, 2010, vol. 107, No. 48, 20661-20665.

* cited by examiner

*Primary Examiner* — Erich A Leeser
(74) *Attorney, Agent, or Firm* — BakerHostetler

(57) ABSTRACT

The present invention relates to functionalized Maleimides and Isomaleimides of general Formula (I) and a process for the preparation thereof, involving [3+2] annulation of α, β-unsaturated aldehydes with carbamoyl alkylates via an enolate pathway to afford highly functionalized compounds of Formula (I);

(I)

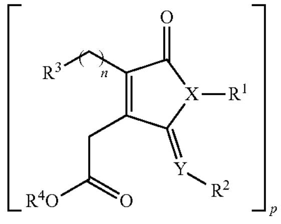

.

16 Claims, 1 Drawing Sheet

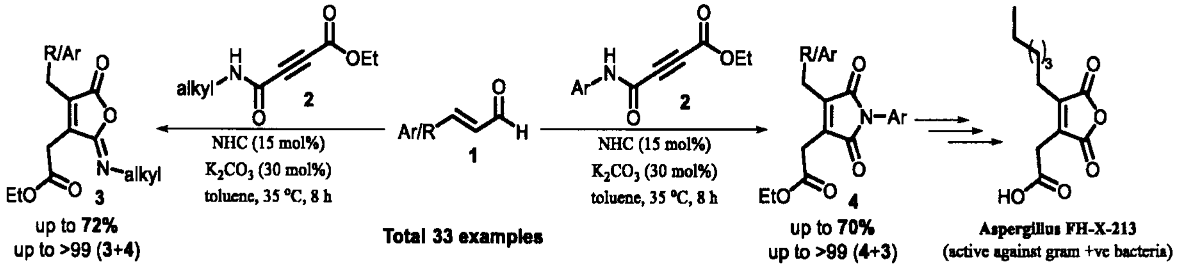
NHC (15 mol%)
$K_2CO_3$ (30 mol%)
toluene, 35 °C, 8 h
NHC (15 mol%)
$K_2CO_3$ (30 mol%)
toluene, 35 °C, 8 h
up to 72%
up to >99 (3+4)
Total 33 examples
up to 70%
up to >99 (4+3)
Aspergillus FH-X-213
(active against gram +ve bacteria)

FUNCTIONALIZED MALEIMIDES AND ISOMALEIMIDES AND A PROCESS FOR PREPARATION THEREOF

FIELD OF INVENTION

The present invention relates to functionalized Maleimides and Isomaleimides of general Formula (I) and a process for preparation thereof. More particularly, the present invention relates to functionalized Maleimides and Isomaleimides of general Formula (I) and process for the preparation thereof, involving [3+2] annulation of α,β-unsaturated aldehydes with carbamoyl alkylates via an enolate pathway to afford highly functionalized compounds of Formula (I).

BACKGROUND AND PRIOR ART

Organo catalysis by N-hetrocyclic carbenes (NHCs) is a synthetic tool of contemporary interest. It has witnessed remarkable growth in the past decade due to its effectiveness in constructing several scaffolds useful in pharmaceutical and material applications under milder and environmentally friendly reaction conditions from simple and readily available starting materials.

The NHC reaction follows either by acyl anion or homoenolate pathway which are well studied and documented in the literature, however the enolate pathway is relatively less explored.

Several works of the past are compared in the scheme presented below:

Previous works:

(1)

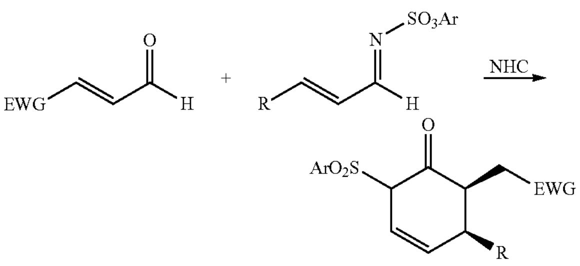

Bode et al. JACS 2006

(2)

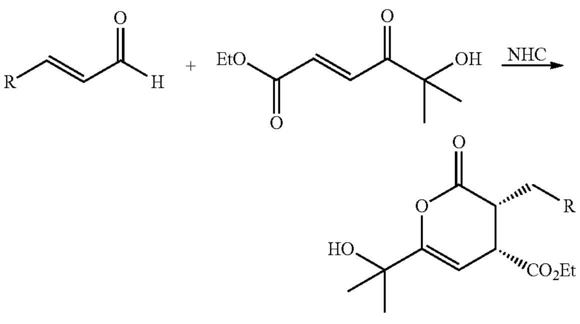

Bode et al. PNAS 2010

(3)

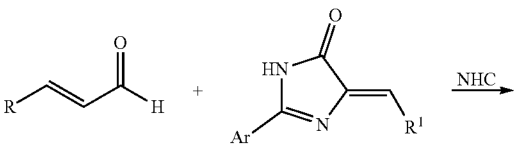

-continued

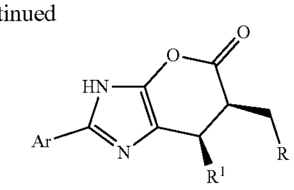

Scheidt et al, ACIE 2013

Present Work:

(4)

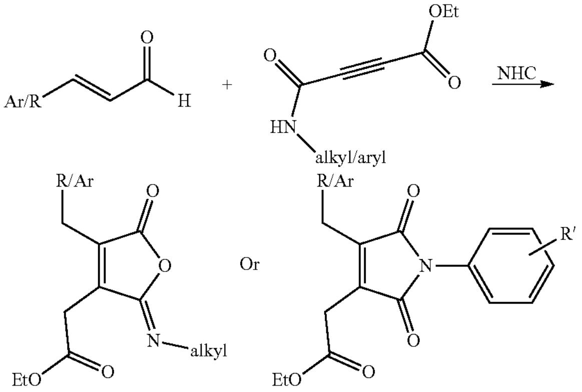

Heterocycles are common structural motifs in the bioactive natural products and several marketed drugs. Nitrogen heterocycles in particular the imide are one of the privileged heterocylic scaffolds found in many bioactive molecules, natural products, drugs or advanced materials. The imides themselves are most often cyclic and the natural products containing them tend to be bioactive.

Since the 1950s, several synthetic methods for their preparation have been disclosed; however, novel facile method is still desired.

The present inventors found that there is a scope to employ relatively less exploited NHC reactivity and therefore endeavored to develop a novel protocol for the construction of functionalized maleimides and isomaleimides utilizing the rarely explored intermolecular reaction of the NHC-bounded enolates from α,β-unsaturated aldehydes with carbamoyl propiolate as the activated electrophilic coupling partner.

OBJECTIVE OF THE INVENTION

The primary objective of the present invention is to provide a functionalized maleimides and isomaleimides of Formula (T) with antimicrobial and anti-cancer activity.

The other objective of the present invention is to provide an efficient N-heterocyclic carbene (NHC)-catalyzed [3+2] annulation of α,β-unsaturated aldehydes of Formula II with carbamoyl alkylates of Formula III via an enolate pathway leading to construction of highly functionalized compounds of Formula (I).

SUMMARY OF THE INVENTION

In accordance with the above, the present invention provides novel highly functionalized maleimides and isomaleimides of the Formula (I), (I)

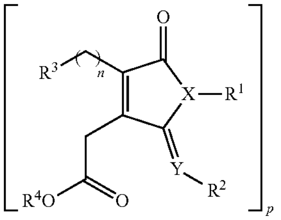

wherein, X and Y independently of each other represent the heteroatom selected from nitrogen or oxygen;

$R^1$, $R^2$ and $R^3$ independently of each other represent unsubstituted or substituted alkyl, unsubstituted or substituted cycloalkyl, unsubstituted or substituted carbocycle, unsubstituted or substituted benzyl, unsubstituted or substituted aryl, and unsubstituted or substituted heterocyclyl;

$R^4$ independently of each other represent hydrogen or $C_{1-4}$ alkyl;

'n' is the integer 1 to 9;

'p' is the integer 1, 2 with the proviso, when 'X' is oxygen, 'Y' is nitrogen and $R^1$ is absent;

when 'Y' is oxygen, 'X' is nitrogen and $R^2$ is absent;

when 'p' is 2, the compound is a bisimide or its congeners at $R^2$;

excluding the compounds wherein,

'X', 'Y', are oxygen, $R^1$ and $R^2$ are absent, $R^3$ is methyl, 'n' is the integer 5 and $R^4$ is hydrogen;

'X' is nitrogen, 'Y is oxygen, $R^1$ is p-tolyl, $R^3$ is methyl, 'n' is the integer 5 and $R^4$ is ethyl.

In an aspect, the present invention provides a process for preparation of the compounds of Formula (I) comprising N-heterocyclic carbene (NHC)-catalyzed [3+2] annulation of α,β-unsaturated aldehydes of Formula (II), (II)

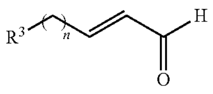

wherein $R^3$ independently of each other represent the groups selected from hydrogen, unsubstituted or substituted $C_1$-$C_{10}$ alkyl, unsubstituted or substituted $C_1$-$C_{10}$ cycloalkyl, unsubstituted or substituted carbocycle, unsubstituted or substituted benzyl, unsubstituted or substituted aryl, and unsubstituted or substituted heterocyclyl, and 'n' represents the integer 1 to 9;

with carbamoyl alkylates of Formula (III), (III)

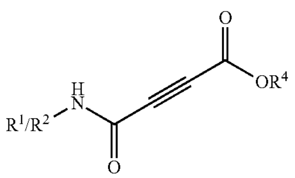

wherein $R^1$ or $R^2$ represent the groups selected from unsubstituted or substituted alkyl, unsubstituted or substituted cycloalkyl, unsubstituted or substituted carbocycle, unsubstituted or substituted benzyl, unsubstituted or substituted aryl, and unsubstituted or substituted heterocyclyl; and $R^4$ independently of each other represent hydrogen or $C_{1-4}$ alkyl;

in the presence of NHC catalyst, base and the solvent at a temperature in the range of 30-40° C. for a period in the range of 8-9 hrs.

The pre-catalyst N-heterocyclic carbene (NHC) for the reaction is selected from the precursors NHC-A to NHC-J shown below:

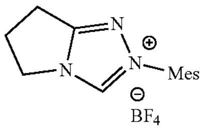

A

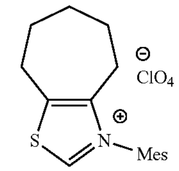

B

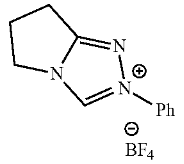

C

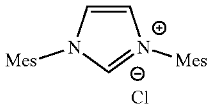

D

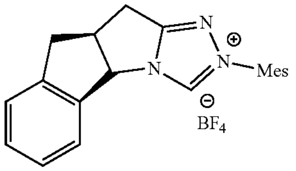

E

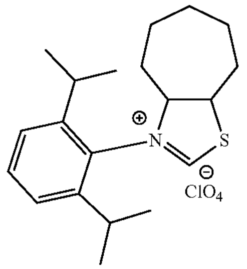

F

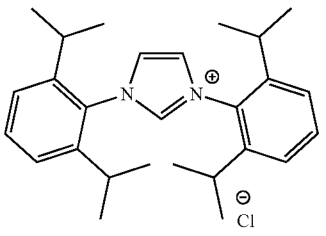

G

-continued

H

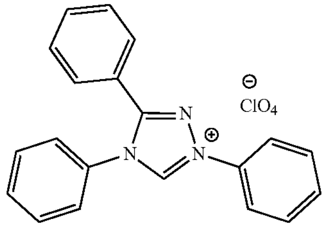

I

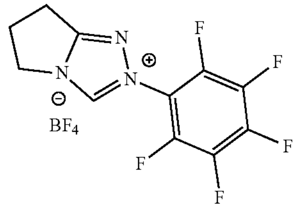

J

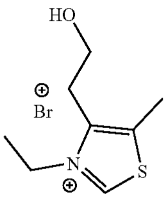

In yet another embodiment, the present invention relates to synthesis of the known natural product *Aspergillus* FH-X-213 which comprises;

a) subjecting trans-2-octenal and ethyl 4-oxo-4-(p-tolylamino)but-2-ynoate (2g) to NHC catalyzed [3+2] annulation in presence of $K_2CO_3$ in toluene at ambient temperature to obtain Ethyl 2-(4-hexyl-2,5-dioxo-1-(p-tolyl)-2,5-dihydro-1H-pyrrol-3-yl)acetate (4aj) and its isomer ethyl (Z)-2-(4-hexyl-5-oxo-2-(p-tolylimino)-2,5-dihydrofuran-3-yl)acetate (3aj);

b) evaporating toluene in vacuum and refluxing the residue in THF:methanol (1:2) and aq. KOH followed by purification to obtain the desired product.

In yet another aspect, the present invention provides the pharmaceutical composition containing highly functionalized maleimides and isomaleimides of Formula (I) together with acceptable excipients.

In another aspect, the functionalized maleimides and isomaleimides of Formula (I) are useful as antimicrobials and anti-cancer agents.

DETAILED DESCRIPTION OF THE INVENTION

The following invention describes in particular the preferred and optional embodiments so that the various aspects therein can be more clearly understood and appreciated.

The term "alkyl" means a straight chain or branched saturated or unsaturated alkyl chain with 1-15, preferably 1-10 C-atoms which may carry one or more substituents;

The term "cycloalkyl" denotes a saturated, cyclic hydrocarbon group with 3-12, preferably 5-7, C-atoms which may carry one or more substituents;

The term "aryl" denotes a mononuclear or dinuclear or polynuclear aromatic group which may carry one or more substituents;

The term "heterocyclyl" means a saturated or unsaturated monocyclic or bicyclic group with 1 or 2 nitrogens, oxygen and/or sulfur atoms which may be substituted;

The term "carbocyclic" means a cyclic alkyl group with 3-12, preferably 5-7 C-atoms which can include one or two carbon-carbon double bonds which may be substituted.

Suitable substituents on the above groups are those which are inert in the reactions involved. In an embodiment, the present invention relates to a novel highly functionalized maleimides and isomaleimides of the Formula (I), (I)

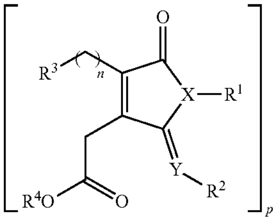

wherein, X and Y independently of each other represent the heteroatom selected from nitrogen or oxygen;

$R^1$, $R^2$ and $R^3$ independently of each other represent unsubstituted or substituted alkyl, unsubstituted or substituted cycloalkyl, unsubstituted or substituted carbocycle, unsubstituted or substituted benzyl, unsubstituted or substituted aryl or unsubstituted or substituted heterocyclyl;

$R^4$ independently of each other represent hydrogen or $C_{1-4}$ alkyl,

'n' is the integer 1 to 9;

'p' is the integer 1, 2 with the proviso, when 'X' is oxygen, 'Y' is nitrogen and $R^1$ is absent;

when 'Y' is oxygen, 'X' is nitrogen and $R^2$ is absent;

when 'p' is 2, the compound is a bisimide or its congeners at $R^2$;

excluding the compounds wherein,

'X', 'Y', are oxygen, $R^1$ and $R^2$ are absent, $R^3$ is methyl, 'in' is the integer 1, 'n' is the integer 5 and $R^4$ is hydrogen;

'X' is nitrogen, 'Y is oxygen, $R^1$ is p-tolyl, $R^3$ is methyl, 'm' is the integer 1, 'n' is the integer 5 and $R^4$ is ethyl.

In an embodiment, the compounds of Formula (I) encompass the isomer compounds, i.e., isomaleimides of Formula (Ia) and maleimides of Formula (Ib) in varying proportion represented below:

(Ia)

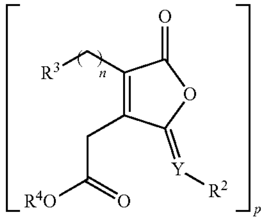

wherein $R^1$, $R^2$ and $R^3$ independently of each other represent unsubstituted or substituted alkyl, unsubstituted or substituted cycloalkyl, unsubstituted or substituted carbocycle, unsubstituted or substituted benzyl, unsubstituted or substituted aryl or unsubstituted or substituted heterocyclyl;

$R^4$ independently of each other represent hydrogen or $C_{1-4}$ alkyl;

'n' is the integer 1 to 9;

'p' is the integer 1, 2 with the proviso, when 'p' is 2, the compound is a bisimide or its congeners at $R^2$.

The compounds of Formula (Ib):

(Ib)

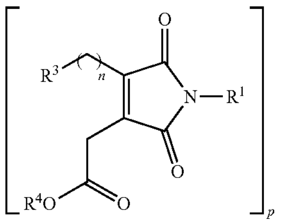

wherein $R^1$, $R^2$ and $R^3$ independently of each other represent unsubstituted or substituted alkyl, unsubstituted or substituted cycloalkyl, unsubstituted or substituted carbocycle, unsubstituted or substituted benzyl, unsubstituted or substituted aryl or unsubstituted or substituted heterocyclyl;

$R^4$ independently of each other represent hydrogen or $C_{1-4}$ alkyl;

'n' is the integer 1 to 9;

'p' is the integer 1, 2 with the proviso, when 'p' is 2, the compound is a bisimide or its congeners at $R^2$;

excluding the compound wherein;

'X' is nitrogen, 'Y is oxygen, $R^1$ is p-tolyl, $R^3$ is methyl, 'n' is the integer 5 and $R^4$ is ethyl.

In another embodiment, the compound of Formula (I) comprises of

| Sr. no. | Compound and IUPAC name |
|---|---|
| 1. | 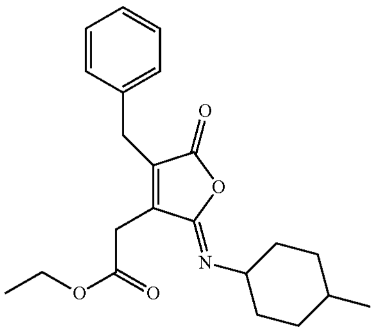<br>(3a)<br>Ethyl (Z)-2-(4-benzyl-2-((4-methylcyclohexyl)imino)-5-oxo-2,5-dibydrofuran-3-yl)acetate (3a); and its maleimide isomer (4a) |

-continued

| Sr. no. | Compound and IUPAC name |
|---|---|
| 2. | 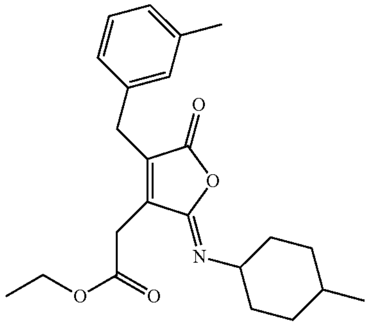<br>(3b) as major<br>Ethyl (Z)-2-(4-(3-methylbenzyl)-2-((4-methylcyclohexyl)imino)-5-oxo-2,5-dihydrofuran-3-yl)acetate (3b); and its maleimide isomer (4b)? |
| 3. | 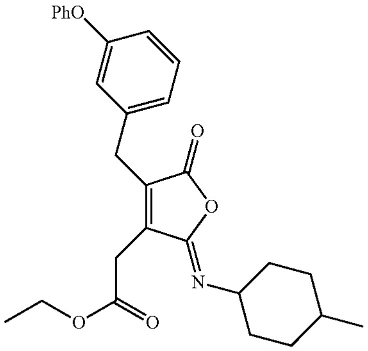<br>(3c) as major<br>Ethyl (Z)-2-(2-((4-methylcyclohexyl)imino)-5-oxo-4-(3-phenoxybenzyl)-2,5-dihydrofuran-3-yl)acetate (3c): and its maleimide isomer (4c) |
| 4. | 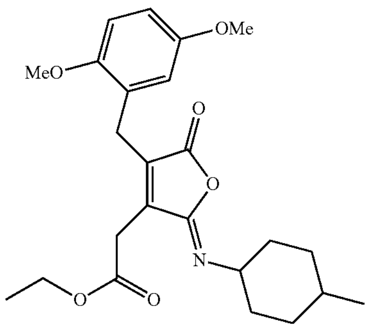<br>(3d) as major<br>Ethyl (Z)-2-(4-(2,5-dimethoxybenzyl)-2-((4-methylcyclohexyl) imino)-5-oxo-2,5-dihydrofuran-3-yl)acetate(3d); and its maleimide isomer (4d) |

-continued

| Sr. no. | Compound and IUPAC name |
|---|---|
| 5. | 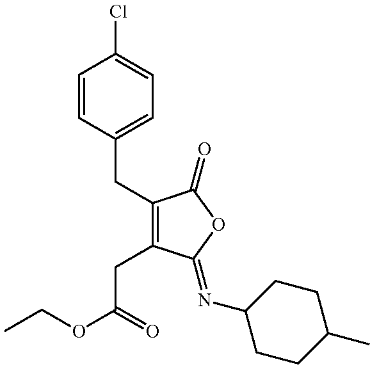<br>(3e) as major<br>Ethyl (Z)-2-(4-(4-chlorobenzyl)-2-((4-methylcyclohexyl)imino)-5-oxo-2,5-dihydrofuran-3-yl)acetate(3e): and its maleimide isomer (4e) |
| 6. | 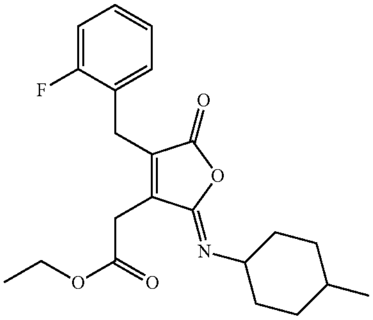<br>(3f) as major<br>Ethyl (Z)-2-(4-(2-fluorobenzyl)-2-((4-methylcyclohexyl)imino)-5-oxo-2,5-dihydrofuran-3-yl)acetate(3f); and its maleimide isomer (4f) |
| 7 | 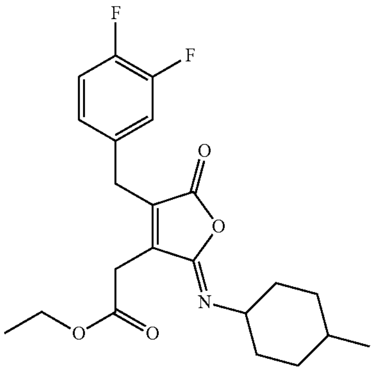<br>(3g) as major<br>Ethyl (Z)-2-(4-(3,4-difluorobenzyl)-2-((4-methyl cyclohexyl)imino)-5-oxo-2,5-dihydrofuran-3-yl)acetate(3g); and its maleimide isomer (4g) |

-continued

| Sr. no. | Compound and IUPAC name |
|---|---|
| 8. | 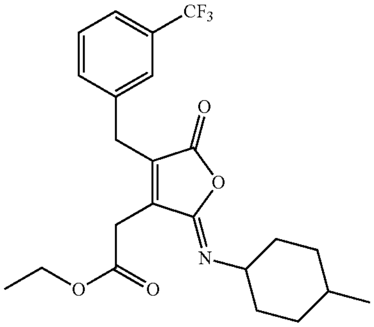<br>(3h) as major<br>Ethyl (Z)-2-(2-((4-methylcyclohexyl)imino)-5-oxo-4-(3-(trifluoromethyl)benzyl)-2,5-dihydrofuran-3-yl)acetate(3h); and its maleimide isomer (4h) |
| 9. | 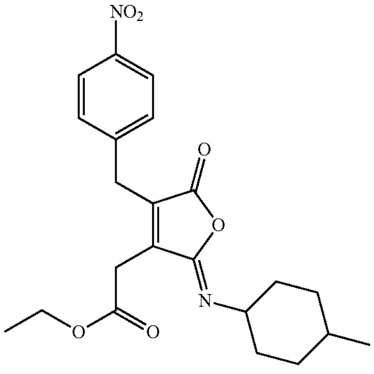<br>(3i) as major<br>Ethyl (Z)-2-(2-((4-methyl cyclohexyl)imino)-4-(4-nitrobenzyl)-5-oxo-2,5-dihydrofuran-3-yl)acetate(3i); and its maleimide isomer (4i) |
| 10. | 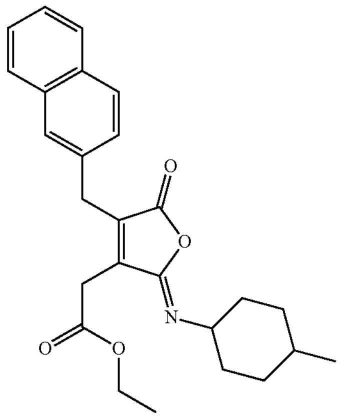<br>(3j) as major<br>Ethyl (Z)-2-(2-((4-methylcyclohexyl)imino)-4-(naphthalen-2-ylmethyl)-5-oxo-2,5-dihydrofuran-3-yl)acetate(3j); and its maleimide isomer (4j) |

-continued

| Sr. no. | Compound and IUPAC name |
|---|---|
| 11. | 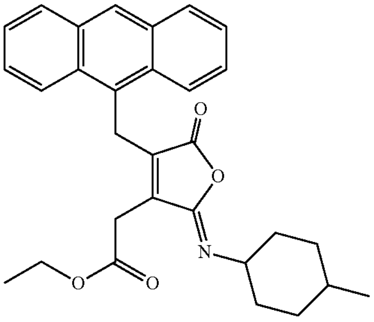 (3k) as major Ethyl (Z)-2-(4-(anthracen-9-ylmethyl)-2-((4-methyl cyclohexyl)imino)-5-oxo-2,5-dihydrofuran-3-yl)acetate (3k); and its maleimide isomer 4(k) |
| 12. | 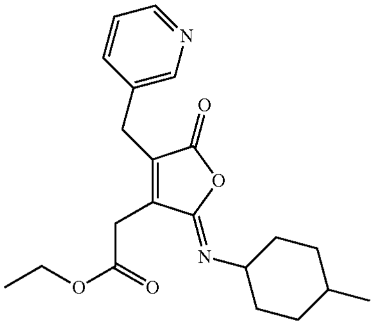 (3l) as major Ethyl (Z)-2-(2-((4-methylcyclohexyl)imino)-5-oxo-4-(pyridin-3-ylmethyl)-2,5-dihydrofuran-3-yl)acetate (3l); and its maleimide isomer (4l). |
| 13. | 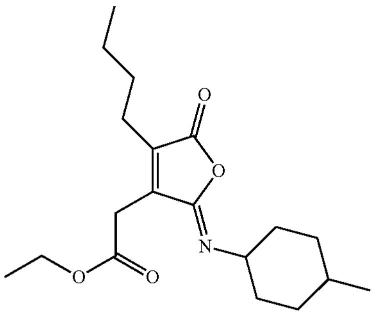 (3m) as major Ethyl (Z)-2-(4-butyl-2-((4-methylcyclohexyl)imino)-5-oxo-2,5-dihydrofuran-3-yl)acetate (3m); and its maleimide isomer (4m) |

-continued

| Sr. no. | Compound and IUPAC name |
|---|---|
| 14. | 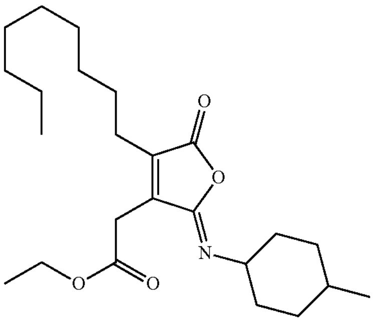 (3n) as major Ethyl (Z)-2-(2-((4-methylcyclohexyl)imino)-4-nonyl-5-oxo-2,5-dihydrofuran-3-yl) acetate (3n); and its maleimide isomer (4n) |
| 15. | 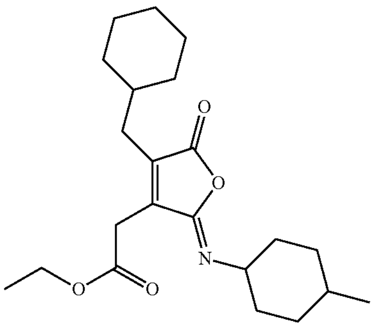 (3o) as major Ethyl (Z)-2-(4-(cyclohexylmethyl)-2-((4-methylcyclohexyl)imino)-5-oxo-2,5-dihydrofuran-3-yl) acetate (3o); and its maleimide isomer (4o) |
| 16. | 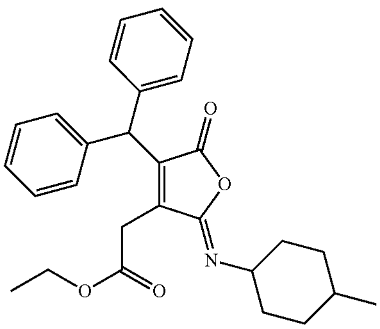 (3p) as major Ethyl (Z)-2-(4-benzhydryl-2-((4-methylcyclohexyl)imino)-5-oxo-2,5-dihydrofuran-3-yl)acetate (3p); and its maleimide isomer (4p) |

-continued

| Sr. no. | Compound and IUPAC name |
|---|---|
| 17. | 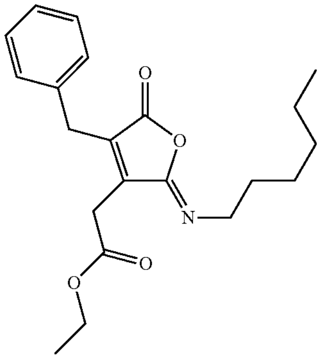<br>(3q) as major<br>Ethyl (Z)-2-(4-benzyl-2-(hexylimino)-5-oxo-2,5-dihydrofuran-3-yl)acetate (3q); and its maleimide isomer (4q) |
| 18. | 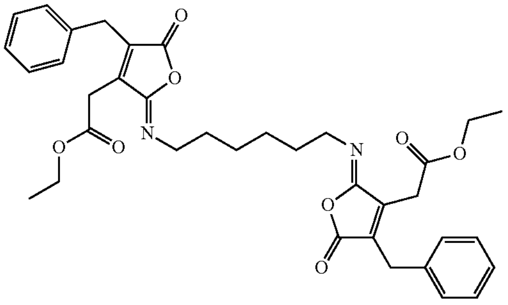<br>(3r) as major<br>Diethyl 2,2′-((2Z,2′-Z)-(hexane-1,6-diylbis(azaneylylidene))bis(4-benzyl-5-oxo-2,5-dihydrofuran-3-yl-2-ylidene))diacetate (3r); and its maleimide isomer (4r) |
| 19. | 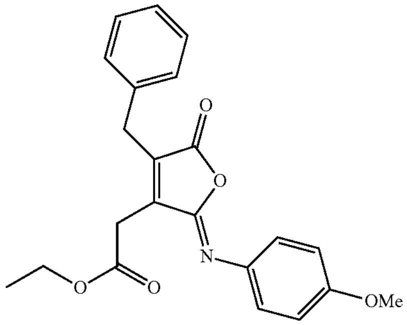<br>(3s)<br>Ethyl (Z)-2-(4-benzyl-2-((4-methoxyphenyl)imino)-5-oxo-2,5-dihydrofuran-3-yl)acetate (3s); and its maleimide isomer (4s) |

-continued

| Sr. no. | Compound and IUPAC name |
|---|---|
| 20. | 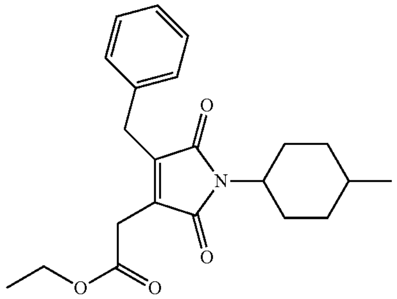<br>(4a)<br>Ethyl 2-(4-benzyl-1-(4-methylcyclohexyl)-2,5-dioxo-2,5-dihydro-1H-pyrrol-3-yl)acetate (4a). |
| 21 | 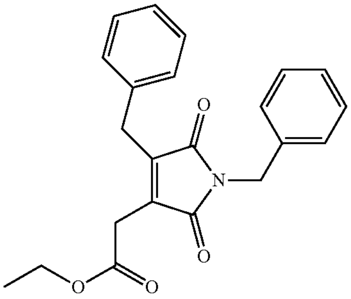<br>(4t) as major<br>Ethyl 2-(1,4-dibenzyl-2,5-dioxo-2,5-dihydro-1H-pyrrol-3-yl) acetate (4t). |
| 22. | 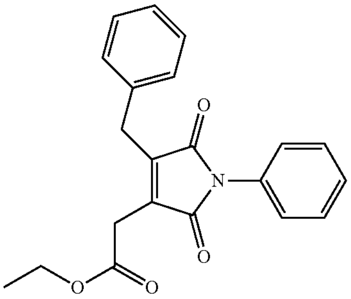<br>(4u) as major<br>Ethyl 2-(4-benzyl-2,5-dioxo-1-phenyl-2,5-dihydro-1H-pyrrol-3-yl) acetate (4u); and its isomaleimide isomer (3u) |
| 23. | 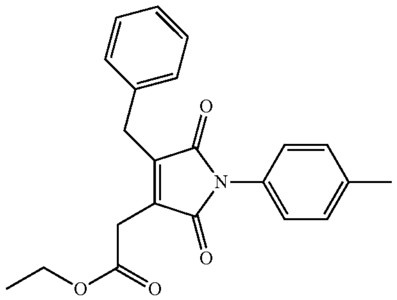<br>(4v) as major<br>Ethyl 2-(4-benzyl-2,5-dioxo-1-(p-tolyl)-2,5-dihydro-1H-pyrrol-3-yl)acetate (4v); and its isomaleimide isomer (3v) |

-continued

| Sr. no. | Compound and IUPAC name |
|---|---|
| 24 | 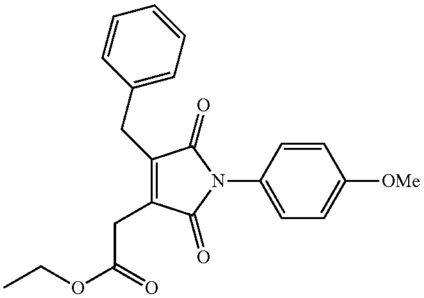<br>(4w) as major<br>Ethyl 2-(4-benzyl-1-(4-methoxyphenyl)-2,5-dioxo-2,5-dihydro-1H-pyrrol-3-yl)acetate (4w); and its isomaleimide isomer (3w) |
| 25. | 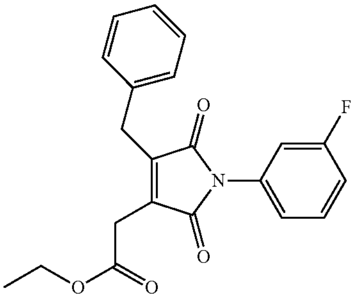<br>(4x) as major<br>Ethyl 2-(4-benzyl-1-(3-fluorophenyl)-2,5-dioxo-2,5-dihydro-1H-pyrrol-3-yl)acetate (4x); and its isomaleimide isomer (3x). |
| 26 | 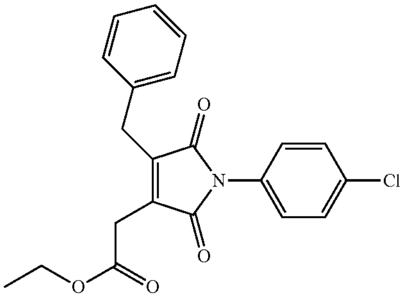<br>(4y) as major<br>Ethyl 2-(4-benzyl-1-(4-chlorophenyl)-2,5-dioxo-2,5-dihydro-1H-pyrrol-3-yl)acetate (4y); and its isomaleimide isomer (3y) |
| 27. | 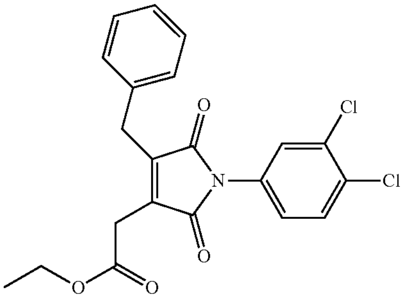<br>(4z) as major<br>Ethyl 2-(4-benzyl-1-(3,4-dichlorophenyl)-2,5-dioxo-2,5-dihydro-1H-pyrrol-3-yl)acetate (4z); and its isomaleimide isomer (3z) |

-continued

| Sr. no. | Compound and IUPAC name |
|---|---|
| 28 | 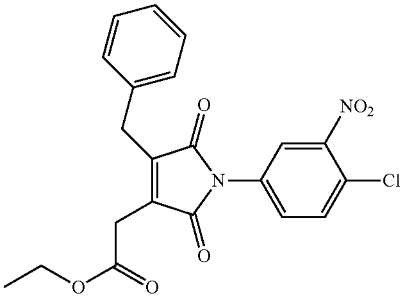<br>(4aa) as major<br>Ethyl 2-(4-benzyl-1-(4-chloro-3-nitrophenyl)-2,5-dioxo-2,5-dihydro-1H-pyrrol-3-yl)acetate (4aa); and its isomaleimide isomer (3aa) |
| 29. | 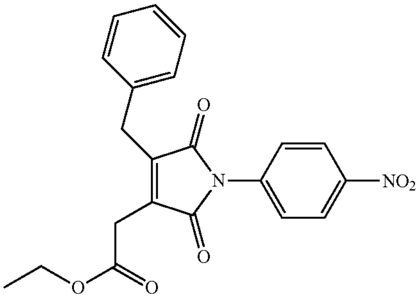<br>(4ab) as major<br>Ethyl 2-(4-benzyl-1-(4-nitrophenyl)-2,5-dioxo-2,5-dihydro-1H-pyrrol-3-yl)acetate(4ab); and its isomaleimide isomer (3ab) |
| 30 | 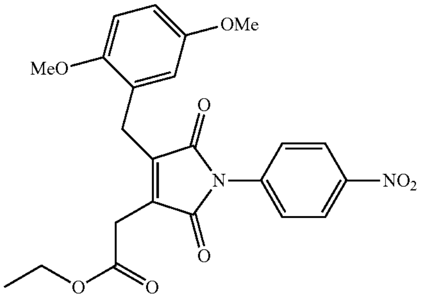<br>(4ac)<br>Ethyl 2-(4-(2,5-dimethoxybenzyl)-1-(4-nitrophenyl)-2,5-dioxo-2,5-dihydro-1H-pyrrol-3-yl)acetate (4ac); and its isomer (3ac) |

-continued

| Sr. no. | Compound and IUPAC name |
|---|---|
| 31 | 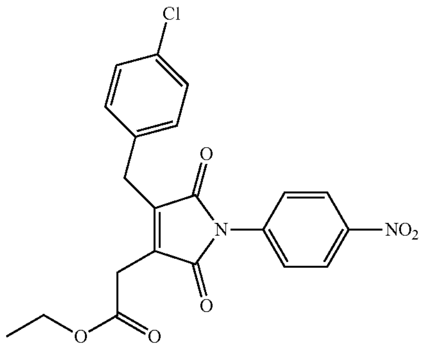<br>(4ad) as major<br>Ethyl 2-(4-(4-chlorobenzyl)-1-(4-nitrophenyl)-2,5-dioxo-2,5-dihydro-1H-pyrrol-3-yl)acetate (4ad); and its isomaleimide isomer (3ad) |
| 32 | 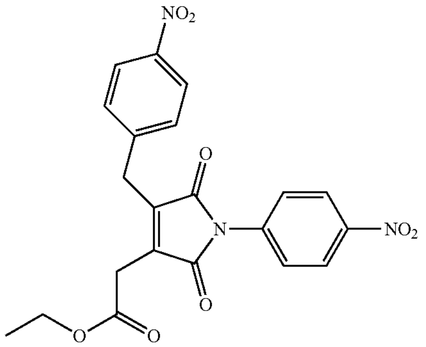<br>(4ae) as major<br>Ethyl 2-(4-(4-nitrobenzyl)-1-(4-nitrophenyl)-2,5-dioxo-2,5-dihydro-1H-pyrrol-3-yl)acetate (4ae); and its isomaleimide isomer (3ae) |
| 33. | 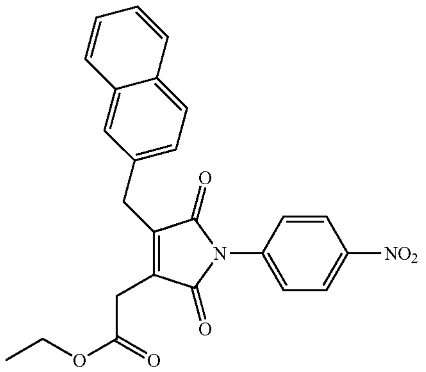<br>(4af) as major<br>Ethyl 2-(4-(naphthalen-2-ylmethyl)-1-(4-nitrophenyl)-2,5-dioxo-2,5-dihydro-1H-pyrrol-3-yl)acetate (4af); and its isomaleimide isomer (3af) |

-continued

| Sr. no. | Compound and IUPAC name |
|---|---|
| 34 | 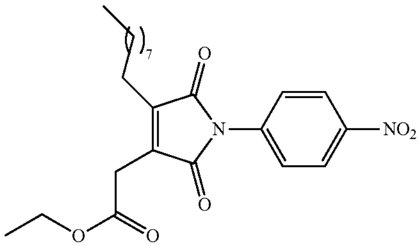<br>(4ah) as major<br>Ethyl 2-(1-(4-nitrophenyl)-4-nonyl-2,5-dioxo-2,5-dihydro-1H-pyrrol-3-yl)acetate (4ah); and its isomalcimide isomer (3ah) |
| 35. | 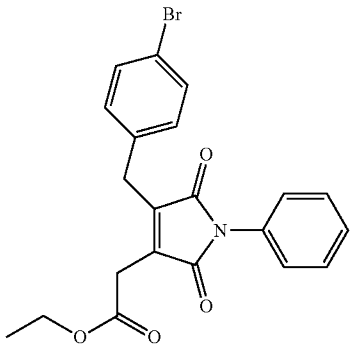<br>(4ai) as major<br>Ethyl 2-(4-(4-bromobenzyl)-2,5-dioxo-1-phenyl-2,5-dihydro-1H-pyrrol-3-yl)acetate (4ai); and its isomaleimide isomer (3ai) |

In another embodiment, the present invention relates to a process for preparation of highly functionalized maleimides and isomaleimides of general Formula (I) comprising N-heterocyclic carbene (NHC)-catalyzed [3+2] annulation of α,β-unsaturated aldehydes of Formula (II),

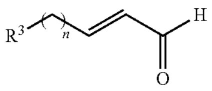

(II)

wherein $R^3$ independently of each other represent the groups selected from unsubstituted or substituted alkyl, unsubstituted or substituted cycloalkyl, unsubstituted or substituted carbocycle, unsubstituted or substituted benzyl, unsubstituted or substituted aryl or unsubstituted or substituted heterocyclyl; and 'n' represents the integer 1 to 9;

with carbamoyl alkylates of Formula (III),

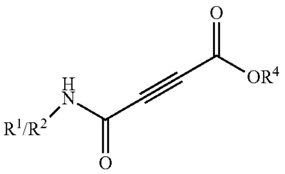

(III)

wherein $R^1$ or $R^2$ represent the groups selected from unsubstituted or substituted alkyl, unsubstituted or substituted cycloalkyl, unsubstituted or substituted carbocycle, unsubstituted or substituted benzyl, unsubstituted or substituted aryl or unsubstituted or substituted heterocyclyl; and $R^4$ represent hydrogen or $C_{1-4}$ alkyl;

in presence of NHC precursors, base and the solvent at a temperature in the range of 30-40° C. for a period in the range of 8-9 hours to yield the desired imides of Formula (I).

The pre-catalyst N-heterocyclic carbene (NHC) for the reaction is selected from the precursors NHC-A to NHC-J shown below:

A

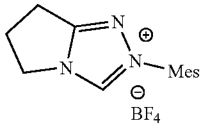

B

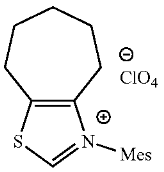

C

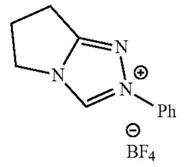

D

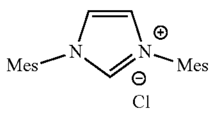

E

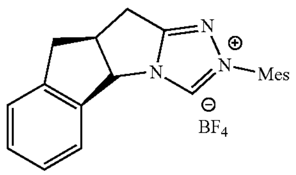

F

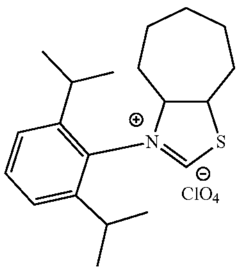

-continued

G

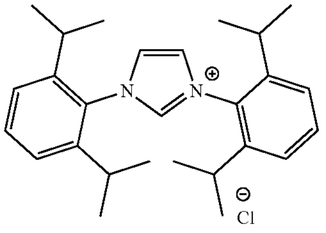

H

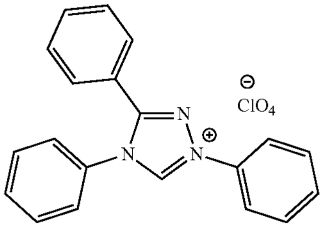

I

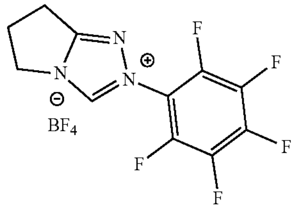

J

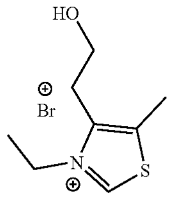

The base for the process is selected from inorganic base such as carbonates or bicarbonates of alkali and alkaline earth metals, preferably carbonates of alkali metals. In particularly useful embodiment base is potassium carbonate;

Solvent is selected from polar or non-polar protic or aprotic aliphatic or aromatic solvent. In particularly useful embodiment, solvent is toluene;

The temperature for the reaction is in the range of 30-40° C.

In an embodiment, the process of the present invention results in the formation of compound of Formula (I) which encompasses the isomer compounds, i.e., isomaleimides of Formula (Ia) and maleimides of Formula (Ib) in varying proportion represented below:

(Ia)

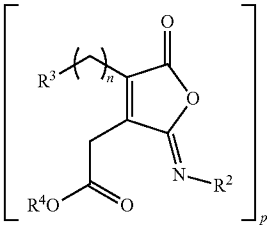

wherein $R^1$, $R^2$ and $R^3$ independently of each other represent unsubstituted or substituted alkyl, unsubstituted or substituted cycloalkyl, unsubstituted or substituted carbocycle, unsubstituted or substituted benzyl, unsubstituted or substituted aryl or unsubstituted or substituted heterocyclyl; $R^4$ represent hydrogen or $C_{1-4}$ alkyl;

'n' is the integer 1 to 9;

'p' is the integer 1, 2 with the proviso, when 'p' is 2, the compound is a bisimide or its congeners at $R^2$.

The compounds of Formula (Ib):

(Ib)

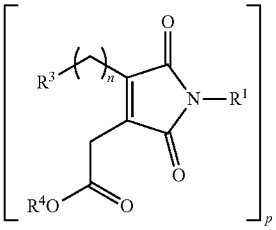

wherein $R^1$, $R^2$ and $R^3$ independently of each other represent unsubstituted or substituted alkyl, unsubstituted or substituted cycloalkyl, unsubstituted or substituted carbocycle, unsubstituted or substituted benzyl, unsubstituted or substituted aryl or unsubstituted or substituted heterocyclyl; $R^4$ represent hydrogen or $C_{1-4}$ alkyl;

'n' is the integer 1 to 9;

'p' is the integer 1,2 with the proviso, when 'p' is 2, the compound is a bisimide or its congeners at $R^2$;

excluding the compound wherein,

'X' is nitrogen, 'Y is oxygen, $R^1$ is p-tolyl, $R^3$ is methyl 'n' is the integer 5 and $R^4$ is ethyl.

In yet another embodiment, the present invention relates to a synthesis of the natural product *Aspergillus* FH-X-213 which comprises:

a) subjecting trans-2-octenal and ethyl 4-oxo-4-(p-tolylamino)but-2-ynoate (2g) to NHC catalyzed [3+2] annulation in presence of $K_2CO_3$ in toluene at ambient temperature to obtain Ethyl 2-(4-hexyl-2,5-dioxo-1-(p-tolyl)-2,5-dihydro-1H-pyrrol-3-yl)acetate (4aj) and its isomer ethyl (Z)-2-(4-hexyl-5-oxo-2-(p-tolylimino)-2,5-dihydrofuran-3-yl)acetate (3aj); and b) evaporating toluene in vacuum and refluxing the residue in THF:methanol (1:2) and aq. KOH followed by purification to obtain the desired product.

The process is shown in Scheme 1 below:

Scheme-1

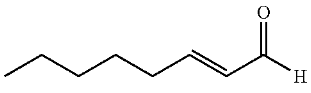

+

1s

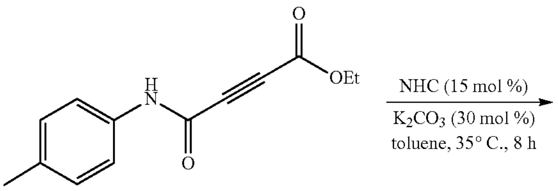

2g

-continued

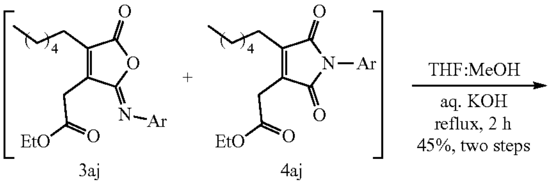

3aj 4aj

Ar = p-MePh

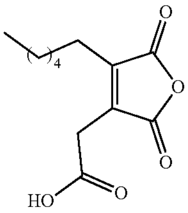

Aspergillus FH-X-213

In another embodiment, the present invention discloses the pharmaceutical composition containing highly functionalized maleimides and isomaleimides of Formula (I) together with acceptable excipients.

In another embodiment, the functionalized maleimides and isomaleimides of Formula (I) are useful as antimicrobials and anti-cancer agents. MTT assay of compounds of Formula (I) is summarized below in Table-1 The compounds were tested against breast cancer cell line at 100 and 300 μM concentrations and % live and % dead cells were determined. Several compounds of Table 1 exhibited almost or more than 50% cell death confirming their potency as anti-cancer compounds.

TABLE 1

| Compound details | MCF-7 | STDEV | % CV | % Live cells | % Dead cells |
|---|---|---|---|---|---|
| 3f | 100 uM | 0.05 | 19.69 | 73.42 | 26.58 |
| | 300 uM | 0.02 | 13.36 | 50.38 | 49.62 |
| 3h | 100 uM | 0.01 | 8.17 | 50.86 | 49.14 |
| | 300 uM | 0.01 | 4.06 | 39.06 | 60.94 |
| 3e | 100 uM | 0.01 | 4.50 | 54.70 | 45.30 |
| | 300 uM | 0.01 | 3.43 | 46.26 | 53.74 |
| 3k | 100 uM | 0.04 | 17.22 | 72.55 | 27.45 |
| | 300 uM | 0.02 | 8.04 | 66.99 | 33.01 |
| 3j | 100 uM | 0.01 | 6.03 | 48.27 | 51.73 |
| | 300 uM | 0.02 | 12.70 | 40.31 | 59.69 |
| 3d | 100 uM | 0.04 | 16.89 | 67.08 | 32.92 |
| | 300 uM | 0.00 | 1.82 | 45.59 | 54.41 |
| 3c | 100 uM | 0.03 | 12.82 | 67.08 | 32.92 |
| | 300 uM | 0.01 | 5.34 | 65.16 | 34.84 |
| 3p | 100 uM | 0.03 | 13.40 | 56.53 | 43.47 |
| | 300 uM | 0.02 | 9.19 | 48.94 | 51.06 |
| 3g | 100 uM | 0.01 | 4.92 | 73.61 | 26.39 |
| | 300 uM | 0.01 | 4.57 | 52.78 | 47.22 |

In an embodiment, the present invention provides novel functionalized maleimides and isomaleimides of Formula (I) useful in the construction of related natural products and drugs.

General reaction of NHC annulation via enolate pathway is given below:

Scheme-2

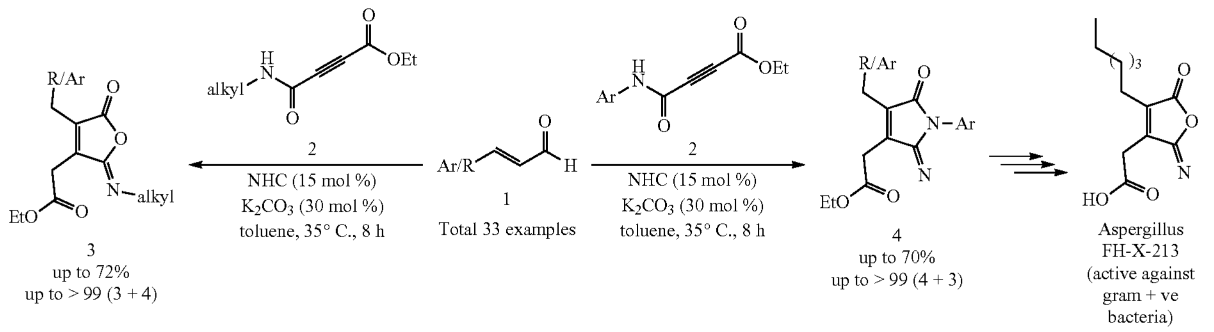

EXPERIMENTAL

General Information:

All reagents and solvents were used as received from commercial sources unless otherwise noted. All experiments were carried out in Schlenk tube with side arm. Precoated plates (silica gel 60 PF254, 0.25 mm or 0.5 mm) were utilized for thin-layer chromatography (TLC). Visualization of the developed TLC plate was performed by irradiation with UV light. Column chromatographic purifications were carried out on flash silica gel (240-400 mesh) using ethyl acetate and petroleum ether as eluents. The $^1H$ and $^{13}C$ NMR spectra were recorded on 200/400/500 and 100/125 MHz NMR spectrometers, respectively, in $CDCl_3$. Chemical shifts were reported as 6 values from standard peaks. The $^{13}C$ NMR spectra of compounds 4x, 4aa, and 4ac show one carbon less because of peak overlapping. The melting points were recorded on a Buchi instrument and are uncorrected. High-resolution mass spectrometry (HRMS) was performed on a TOF/Q-TOF mass spectrometer. All carbamoyl propiolate starting materials were prepared according to literature procedures [Pandya, V.: Mhaske, S. B. *Org. Lett.* 2018, 20, 1483] starting from the corresponding isocyanate and ethyl propiolate and the structures were confirmed by literature reports. New compounds were characterized completely. All the aldehydes were purchased from commercial source and used without further purification.

EXPERIMENTAL PROCEDURES

Example 1

[A]—General Procedure for Synthesis of Carbamoyl Propiolates.

All the carbamoyl propiolates were prepared according to the reported procedure [Pandya, V.; Mhaske, S. B. *Org. Lett.* 2018, 20, 1483]. Ethyl propiolate (1.0 equivalent) was dissolved in THF (5 ml) and the solution was cooled to −78° C., followed by the slow addition of n-BuLi (1.2 equiv, 1.5 M in hexane). The mixture was stirred for 30 min and a solution of the corresponding isocyanate (500 mg, 1.0 equivalent) in THF (5 mL) was added dropwise. The reaction mixture was then stirred for 3-5 h at same temperature and acetic acid (1 mL) was added to quench the reaction after completion. The reaction mixture was allowed to warm to room temperature, water was added, and the aqueous layer was extracted with ethyl acetate (20 mL×3). The combined organic extract was dried over anhydrous $Na_2SO_4$ and removal of solvent gave a residue that was subjected to flash column chromatography on silica-gel using ethyl acetate:petroleum ether (1:5) as eluent to afford the corresponding compounds.

[B]— General Procedure for Selective Synthesis of Isomaleimides Using Alkyl Substituted Carbamoyl Propiolate (3a-s):

An oven-dried Schlenk tube equipped with a magnetic stirring bar was charged with carbamoyl propiolate (0.1 mmol, 1 equiv), aldehyde (0.15 mmol, 1.5 equivalent), NHC-pre catalyst (6.3 mg, 0.015 mmol, 15 mol %), and $K_2CO_3$ (4.1 mg, 0.030 mmol, 30 mol %) under argon atmosphere. To this mixture, toluene (1.0 mL) was added and the Schlenk tube was backfilled with argon and heated at 35° C. in a preheated oil bath. The progress of the reaction was monitored using TLC analysis. After 8 hours, the reaction was stopped, and solvent was evaporated under the reduced pressure. The crude reaction mixture was purified by flash column chromatography using ethyl acetate and petroleum ether as eluents.

[C]— General Procedure for Selective Synthesis of Maleimides Using Aryl Substituted Carbamoylpropiolate (4u-ai):

An oven-dried Schlenk tube equipped with a magnetic stirring bar was charged with carbamoyl propiolate (0.1 mmol, 1 equivalent), aldehyde (0.15 mmol, 1.5 equivalent), NHC-pre catalyst (6.3 mg, 0.015 mmol, 15 mmol %), and $K_2CO_3$ (4.1 mg, 0.030 mmol, 30 mol %) under argon atmosphere. To this mixture, toluene (1.0 mL) was added and the Schlenk tube was backfilled with argon and heated at 35° C. in a preheated oil bath. The progress of the reaction was monitored using TLC analysis. After 8 hours, the reaction was stopped, and solvent was evaporated under the reduced pressure. Acetic acid (1 mL) was added to the crude reaction mixture and heated to 120° C. for 4 hours. After converting all the mixture to single maleimide product, the acetic acid was evaporated and diluted with EtOAc, washed with water, aqueous saturated $Na_2CO_3$ (10 mL×2) and brine. The organic layer was dried over $Na_2SO_4$, concentrated under vacuum, and the crude residue was purified by flash column chromatography using ethyl acetate and petroleum ether as eluents.

Example 2: Preparation of representative compound Ethyl (Z)-2-(4-benzyl-2-((4-methylcyclohexyl)imino)-5-oxo-2,5-dihydrofuran-3-yl)acetate (3a)

An oven-dried Schlenk tube equipped with a magnetic stirring bar was charged with ethyl 4-((4-methylcyclohexyl)

amino)-4-oxobut-2-ynoate (2c, 23.7 mg, 0.1 mmol, 1 equiv), cinnamaldehyde (1a, 20 mg, 0.15 mmol, 1.5 equiv), NHC-precatalyst (6.3 mg, 0.015 mmol, 15 mol %), and $K_2CO_3$ (4.1 mg, 0.030 mmol, 30 mol %) under argon atmosphere. To this mixture, toluene (1.0 mL) was added and the Schlenk tube was backfilled with argon and heated at 35° C. in a preheated oil bath. The progress of the reaction was monitored using TIC analysis. After 8 h, the reaction was stopped, and solvent was evaporated under the reduced pressure. The crude reaction mixture was purified by flash column chromatography using ethyl acetate and petroleum ether as eluents to afford pure isomaleimide product 3a in 66% (24.3 mg).

Example 3: Preparation of representative compound Ethyl 2-(4-benzyl-2,5-dioxo-1-phenyl-2,5-dihydro-1H-pyrrol-3-yl) acetate (4u)

An oven-dried Schlenk tube equipped with a magnetic stirring bar was charged with ethyl 4-oxo-4-(phenylamino) but-2-ynoate (2a, 21.7 mg, 0.1 mmol, 1 equivalent), cinnamaldehyde (1a, 20 mg, 0.15 mmol, 1.5 equivalent), NHC-precatalyst (6.3 mg, 0.015 mmol, 15 mol %), and $K_2CO_3$ (4.1 mg, 0.030 mmol, 30 mol %) under argon atmosphere. To this mixture, toluene (1.0 mL) was added and the Schlenk tube was backfilled with argon and heated at 35° C. in a preheated oil bath. The progress of the reaction was monitored using TLC analysis. After 8 hours, the reaction was stopped, and solvent was evaporated under the reduced pressure. Acetic acid (1 mL) was added to the crude reaction mixture and heated to 120° C. for 4 hours. After converting the mixture to single product, the acetic acid was evaporated and diluted with EtOAc, washed with water, aqueous saturated $Na_2CO_3$ (10 mL×2) and brine. The organic layer was dried over $Na_2SO_4$ concentrated under vacuum, and the crude residue was purified by flash column chromatography using ethyl acetate and petroleum ether as eluents to afford pure maleimide product 4u in 65% (22.6 mg).

Example 4: Procedure for Scale Up Experiment (a): Procedure for Synthesis of 3a:

An oven-dried Schlenk tube equipped with a magnetic stirring bar was charged with ethyl 4-((4-methylcyclohexyl) amino)-4-oxobut-2-ynoate 2c (237 ng, 1 mmol, 1 equivalent), cinnamaldehyde (198 mg, 1.5 mmol, 1.5 equiv), NHC-precatalyst (63 mg, 0.15 mmol, 15 mol %), and $K_2CO_3$ (41 mg, 0.30 mmol, 30 mol %) under argon atmosphere. To this mixture, toluene (10 mL) was added and the Schlenk tube was backfilled with argon and heated at 35° C. in a preheated oil bath. The progress of the reaction was monitored using TLC analysis. After completing the reaction, solvent was evaporated under the reduced pressure. The crude reaction mixture was purified by flash column chromatography using ethyl acetate and petroleum ether as eluents to afford pure isomaleimide product 3a in 60% (221 mg).

(b): Procedure for Synthesis of 4v:

An oven-dried Schlenk tube equipped with a magnetic stirring bar was charged with ethyl 4-oxo-4-(p-tolylamino) but-2-ynoate 2g (230 mg, 1 mmol, 1 equiv), cinnamaldehyde (198 mg, 1.5 mmol, 1.5 equiv), NHC-precatalyst (63 mg, 0.15 mmol, 15 mol %), and $K_2CO_3$ (41 mg, 0.30 mmol, 30 mol %)) under argon atmosphere. To this mixture, toluene (10 mL) was added and the Schlenk tube was backfilled with argon and heated at 35° C. in a preheated oil bath. The progress of the reaction was monitored using TLC analysis. After completing the reaction, solvent was evaporated under the reduced pressure. Acetic acid (10 mL) was added to the crude reaction mixture and heated to 120° C. for 4 h. After converting the mixture to single product, the acetic acid was evaporated and diluted with EtOAc, washed with water, aqueous saturated $Na_2CO_3$ (50 mL×2) and brine. The organic layer was dried over $Na_2SO_4$, concentrated under vacuum, and the crude residue was purified by flash column chromatography using ethyl acetate and petroleum ether as eluents to afford pure maleimide product 4v in 62% (224 rug).

Example 5: Control Experiments to Understand the Mechanism of Reaction (a1)—Experimental Procedure for Reaction of Isomaleimide 3u Under Standard Condition:

An oven-dried Schlenk tube equipped with a magnetic stirring bar was charged with isomaleimide 3u (17.5 mg, 0.05 mmol, 1 equivalent) NHC-precatalyst (3 mg, 0.0075 mmol, 15 mol %), and $K_2CO_3$ (2 mg, 0.015 mmol, 30 mol %) under argon atmosphere. To this mixture, toluene (0.5 mL) was added and the Schlenk tube was backfilled with argon and heated at 35° C. in a preheated oil bath. The reaction was stopped after 8 hours, and compound was purified by passing through the flash column chromatography using ethyl acetate and petroleum ether as eluents to obtain as mixture of 3u and 4u in 92% (16 mg).

(a2)—Experimental Procedure for Reaction of Maleimide 4u Under Standard Condition:

An oven-dried Schlenk tube equipped with magnetic stirring bar was charged with maleimide 4u (17.5 mg, 0.05 mmol, 1 equivalent) NHC-precatalyst (3 mg, 0.0075 mmol, 15 mol %), and $K_2CO_3$ (2 mg, 0.015 mmol, 30 mol %) under argon atmosphere. To this mixture, toluene (0.5 mL) was added and the Schlenk tube was backfilled with argon and heated at 35° C. in a preheated oil bath. The reaction was stopped after 8 hours and found that, all the starting material remained unchanged.

(a3)—Procedure for Synthesis of Maleimide 4a from Corresponding Isomaleimide 3a:

The title compound 4a was prepared according to general procedure [Haval, K. P.; Argade, N. P. *Tetrahedron* 2006, 62, 3557]. A solution of isomaleimide 3a (20 mg) in glacial acetic acid (1 mL) was heated at 120° C. for 4 hours. Acetic acid was evaporated under reduced pressure and the residue was dissolve in ethyl acetate. The organic layer was washed with water, aqueous $Na_2CO_3$ and brine. The organic layer was dried over $Na_2SO_4$, concentrated under vacuum, and the crude residue was purified by flash column chromatography using ethyl acetate and petroleum ether as eluents to afford pure maleimide product 4a in 90% yield (18 mg).

Observation:

The pure isomaleimide 3u was subjected to the standard reaction condition and we observed the mixture of 3u and 4u in 1:5 proportion. However, pure maleimide 4u did not show any change under the standard reaction condition. These experiments indicate the preferred formation of isomaleimides as products of kinetic control and the formation of the thermodynamically stable maleimides via the rearrangement of isomaleimides depending on the nature of the substituent present on the nitrogen.

Example 6: Synthesis of Natural Product *Aspergillus* FH-X-213

Step 1) An oven-dried Schlenk tube equipped with a magnetic stirring bar was charged with carbamoyl propiolate 2g (46 mg, 0.2 mmol, 1 equivalent), trans-2-octenal (38 mg, 0.3 mmol, 1.5 equivalent), NHC-precatalyst (12.5 mg, 0.03 mmol, 15 mol %), and $K_2CO_3$ (8.2 mg, 0.06 mmol, 30 mol %) under argon atmosphere. To this mixture, toluene (2.0 mL) was added and the Schlenk tube was backfilled with argon and heated at 35° C. in a preheated oil bath. The progress of the reaction was monitored using TLC analysis. After completing the reaction, the reaction mixture was passed through the flash column chromatography using ethyl acetate and petroleum ether as eluent and obtained as mixture of compounds, which was utilized for the next step.

Step 2) To a stirred mixture of maleimide and isomaleimide (43 mg) in a THF-methanol mixture (1:2.2 mL) was added 20% aqueous KOH solution (1.5 mL) and the reaction mixture was refluxed for 2 h with stirring. The reaction mixture was concentrated, and the residue was acidified with 2N HCl then extracted with diethyl ether (3×20 mL) and the organic layer was washed with water, brine and dried over $Na_2SO_4$. Concentration of the organic layer in vacuo followed by silica gel column chromatographic purification of the residue with petroleum ether and ethyl acetate furnished the expected product in 22 mg (45% yield over two steps).

Example 7: Characterization Data of Compounds i. Ethyl 4-((4-nitrophenyl)amino)-4-oxobut-2-ynoate (2b)

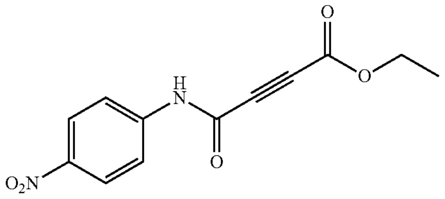 [SMILES: CCOC(=O)C#CC(=O)Nc1ccc([N+](=O)[O-])cc1]

The title compound 2b was prepared according to the general procedure A as yellow solid in 42% yield (335 mg); $R_f$ 0.5 (ethyl acetate:pet. ether, 1:3): mp: 128-130° C.; $^1H$ NMR (400 MHz, $CDCl_3$) δ (ppm) 8.28-8.26 (m, 1H), 8.26 (d, J=9.13 Hz, 2H), 7.74 (d, J=9.01 Hz, 2H), 4.34 (q, J=7.13 Hz, 2H), 1.37 (t, J=7.13 Hz, 3H); HRMS (ESI-TOF) m/z $[M+H]^+$ calcd for $C_{12}H_{11}N_2O_5$ 263.0667, found 263.0674.

ii. Ethyl 4-(hexylamino)-4-oxobut-2-ynoate (2d)

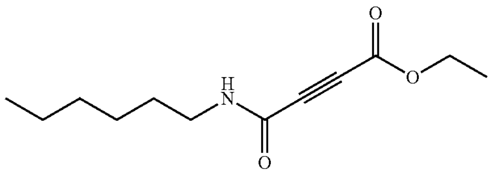 [SMILES: CCCCCCNC(=O)C#CC(=O)OCC]

The title compound 2d was prepared according to the general procedure A as colourless liquid in 62% yield (549 mg); $R_f$ 0.6 (ethyl acetate:pet. ether, 1:3); $^1H$ NMR (400 MHz, $CDCl_3$) δ (ppm) 6.00 (brs, 1H), 4.29 (q, J=7.13 Hz, 2H), 3.36-3.28 (m, 2H), 1.57-1.50 (in, 2H), 1.38-1.29 (m, 9H), 0.92-0.87 (m, 3H); HRMS (ESI-TOF) m/z $[M+H]^+$ calcd for $C_{12}H_{20}NO_3$ 226.1442, found 226.1445.

iii. Diethyl 4,4'-(hexane-1,6-diylbis(azanediyl))bis(4-oxobut-2-ynoate) (2e)

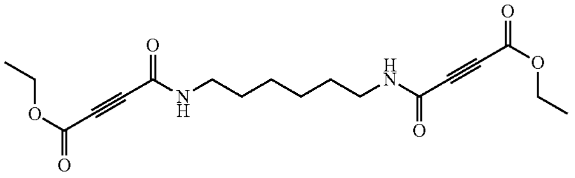 [SMILES: CCOC(=O)C#CC(=O)NCCCCCCNC(=O)C#CC(=O)OCC]

The title compound 2e was prepared according the general procedure A as colourless solid in 60% yield (649 mg); $R_f$ 0.5 (ethyl acetate:pet. ether, 1:2); mp: 91-93° C.; $^1H$ NMR (400 MHz, $CDCl_3$) δ (ppm) 6.38 (br, 2H), 4.28 (q, J=7.1 Hz, 4H), 3.32 (q, J=6.4 Hz, 4H), 1.59-1.52 (m, 4H), 1.37-1.30 (m, 10H); ESI-Mass $(M+H)^+$=365.1.

iv. Ethyl 4-((4-methoxyphenyl)amino)-4-oxobut-2-ynoate (2h)

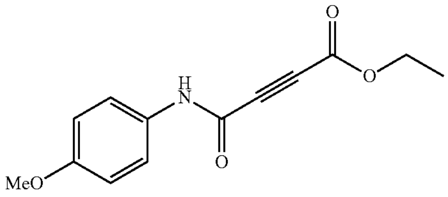 [SMILES: CCOC(=O)C#CC(=O)Nc1ccc(OC)cc1]

The title compound 2h was prepared according to the general procedure A as colourless solid in 57% yield (472 mg); $R_f$ 0.5 (ethyl acetate:pet ether, 1:3); mp: 77-79° C.; $^1H$ NMR (400 MHz, $CDCl_3$) δ (ppm) 7.80 (brs, 1H), 7.45 (dt, 3=9.16 & 2.29 Hz, 2H), 6.88 (dt, 3=9.16 & 2.29 Hz, 2H), 4.31 (q, J=6.87 Hz, 2H), 3.80 (s, 3H), 1.35 (1, J=6.87 Hz, 3H); HRMS (ESI-TOE) m/z $[M+H]^+$ calcd for $C_{13}H_{14}NO_4$ 248.0922, found 248.0928.

v. Ethyl 4-((3-fluorophenyl)amino)-4-oxobut-2-ynoate (2i)

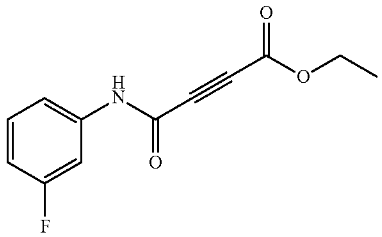 [SMILES: CCOC(=O)C#CC(=O)Nc1cccc(F)c1]

The title compound 2i was prepared according to the general procedure A as yellow liquid in 52% yield (446 rig); $R_f$ 0.5 (ethyl acetate:pet. ether, 1:3); $^1H$ NMR (400 MHz, $CDCl_3$) δ (ppm) 7.91 (brs, 1H), 7.47 (tt, J=10.38 & 2.25 Hz, 1H), 7.35-7.28 (m, 1H), 7.20-7.12 (m, 1H), 6.92-6.85 (m, 1H), 4.33 (q, J=7.13 Hz, 2H), 1.36 (t, J=7.13 Hz, 3H); HRMS (ESI-TOF) m/z $[M+H]^+$ calcd for $C_{12}H_{11}NO_3$ 236.0722, found 236.0727.

vi. Ethyl 4-((3,4-dichlorophenyl)amino)-4-oxobut-2-ynoate (2k)

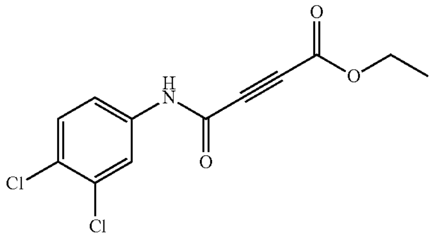 [SMILES: CCOC(=O)C#CC(=O)Nc1ccc(Cl)c(Cl)c1]

The title compound 2k was prepared according to the general procedure A as colourless solid in 51% t yield (387 mg); $R_f$ 0.5 (ethyl acetate:pet. ether, 1:3); mp: 69-71° C.; $^1$H NMR (400 MHz, $CDCl_3$) δ (ppm) 7.95 (brs, 1H), 7.77 (d, J=2.5 Hz, 1H), 742 (d, J=8.63 Hz, 1H), 7.36 (dd, J=8.76 & 2.5 Hz, 1H), 4.33 (q, J: =7.25 Hz, 2H), 1.36 (t, J=7.25 Hz, 3H); ESI-Mass $(M+H)^+$ 286.0.

vii. Ethyl 4-((4-chloro-3-nitrophenyl)amino)-4-oxobut-2-ynoate (2l)

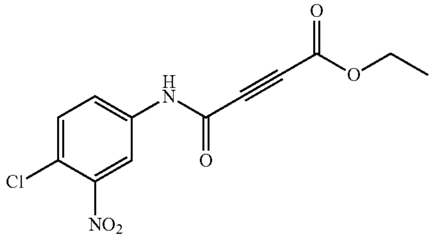 [SMILES: CCOC(=O)C#CC(=O)Nc1ccc(Cl)c([N+](=O)[O-])c1]

The title compound 2l was prepared according to the general procedure A as colourless solid in 44% yield (329 mg); $R_f$ (05 (ethyl acetate:pet, ether, 1:3); mp: 99-101° C.; $^1$H NMR (400 MHz, $CDCl_3$) δ (ppm) 8.53 (brs, 1H), 8.18 (d, J=2.5 Hz, 1H), 7.77 (dd, J=8.75 & 2.63 Hz, 1H), 7.54 (d, J=8.88 Hz, 11-1), 4.34 (q, J=7.13 Hz, 2H), 1.36 (t, J=7.13 Hz, 3H); ESI-Mass $(M+Na)^+$ 319.0.

viii. Ethyl (Z)-2-(4-benzyl-2-((4-methylcyclohexyl) imino)-5-oxo-2,5-dihydrofuran-3-yl)acetate (3a)

The title compound 3a was prepared according to the general procedure B as sticky solid in 66% yield (24 ng, 3a:4a=95:05); Reaction time 8 hours/35° C.; $R_f$ 0.7 (ethyl acetate:pet. ether, 1:4); $^1$H NMR (400 MHz, $CDCl_3$) δ (ppm) 7.35-7.18 (m, 5H) 4.11 (q, J=7.25 Hz, 2H), 3.77 (s, 2H), 3.70-3.76 (m, 1H), 3.44 (s, 2H), 1.76-1.68 (m, 4H), 1.49-1.35 (m, 3H), 1.22 (t, J=6.87 Hz, 3H), 1.08-0.99 (m, 2H), 0.90 (d, J=6.10 Hz, 3H); HRMS (ESI-TOF) m/z $[M+H]^+$ calcd for $C_{22}H_{28}NO_4$, 370.2013; found, 370.2017.

ix. Ethyl (Z)-2-(4-(3-methylbenzyl)-2-((4-methylcyclohexyl)imino)-5-oxo-2,5-dihydrofuran-3-yl)acetate (3b)

The title compound 3b was prepared according to the general procedure B as sticky solid in 65% yield (25 mg, 3b:4b=96:04); Reaction time 8 h/35° C.; $R_f$ 0.7 (ethyl acetate:pet. ether, 1:4); 1H NMR (400 MHz, $CDCl_3$) δ (ppm) 7.19 (t, J=7.44 Hz, 1H), 7.08-6.98 (m, 3H), 4.11 (q, J=7.19 Hz, 2H), 3.81-3.70 (m, 3H), 3.43 (s, 2H), 2.32 (s, 3H), 1.76 (m, 4H), 1.49-1.35 (m, 3H), 1.22 (t, J=7.13 Hz, 3H), 1.08-0.98 (m, 2H), 0.90 (d, J=6.50 Hz, 3H); HRMS (ESI-TOF) m/z [M+H]+ calcd for $C_{23}H_{30}NO_4$ 384.2169; found, 384.2175.

x. Ethyl (Z)-2-(2-((4-methylcyclohexyl)imino)-5-oxo-4-(3-phenoxy benzyl)-2,5-dihydrofuran-3-yl) acetate (3c)

The title compound 3e was prepared according to the general procedure B as sticky solid in 60% yield (28 mg, 3c:4c=95:05); Reaction time 8 hours/35° C., $R_f$ 0.5 (ethyl acetate:pet. ether, 1:4); $^1$H NMR (400 MHz, $CDCl_3$) δ (ppm) 7.38-7.32 (m, 2H), 7.27-7.22 (m, 11H), 7.15-7.08 (m, 1H), 7.02-6.94 (m, 3H), 6.93-6.88 (m, 1H), 6.88-6.84 (m, 1H), 4.11 (q, J=6.87 Hz, 2H), 3.83-3.68 (m, 3H), 3.45 (s, 2H), 1.77-1.67 (m, 4H), 1.51-1.36 (m, 3H), 1.22 (t, J=6.87 Hz, 3H), 1.08-1.0 (m, 2H), 0.91 (d, J=6.87 Hz, 3H); HRMS (ESI-TOF) m/z $[M+H]^+$ calcd for $C_{28}H_{32}NO_5$, 462.2275; found, 462.2281.

xi. Ethyl (Z)-2-(4-(2,5-dimethoxybenzyl)-2-((4-methylcyclohexyl)imino)-5-oxo-2,5-dihydrofuran-3-yl)acetate (3d)

The title compound 3d was prepared according to the general procedure B as sticky solid in 69% yield (30 mg, 3d:4d=99:01); Reaction time 8 hours/35° C.; $R_f$ 0.5 (ethyl acetate:pet. ether, 1:4); $^1$H NMR (400 MHz, $CDCl_3$) δ (ppm) 6.88 (d, J=1.53 Hz, 1H), 6.76 (d, J=2.29 Hz, 2H), 4.10 (q, J=7.25 Hz, 2H), 3.76 (s, 3H), 3.76 (s, 3H), 3.73-3.69 (m, 3H), 3.51 (s, 2H), 1.74-1.8 (m, 4H), 1.46-1.37 (m, 3H), 1.22 (t, J=7.25 Hz, 3H), 1.06-0.99 (m, 2H), 0.9 (m, 3H); HRMS (ESI-TOF) m/z $[M+H]^+$ calcd for $C_{24}H_{32}NO_6$, 430.2224, found, 430.2230.

xii. Ethyl (Z)-2-(4-(4-chlorobenzyl)-2-((4-methylcyclohexyl)imino)-5-oxo-2,5-dihydro furan-3-yl)acetate (3e)

The title compound 3e was prepared according to the general procedure B as sticky solid in 62% yield (25 mg, 3e:4e=97:03); Reaction time 8 hours/35° C.; $R_f$ 0.6 (ethyl acetate:pet. ether, 1:4); $^1$H NMR (400 MHz, $CDCl_3$) δ (ppm) 7.27 (d J=8.25 Hz, 2H), 7.18 (d. J=8.25 Hz, 2H), 4.12 (q, J=7.13 Hz, 2H), 3.80-3.70 (m, 3H), 3.46 (s, 2H), 1.77-1.68 (m, 4H), 1.50-1.35 (m, 3H), 1.23 (t, J=7.13 Hz, 3H), 1.07-1.0 (m, 2H), 0.9 (d, J=6.50 Hz, 3H); HRMS (ESI-TOF) m/z $[M+H]^+$ calcd for $C_{22}H_{27}NO_4Cl$, 404.1623; found, 404.1627.

xiii. Ethyl (Z)-2-(4-(2-fluorobenzyl)-2-((4-methylcyclohexyl)imino)-5-oxo-2,5-dihydro furan-3-yl) acetate (3f)

The title compound 3f was prepared according to the general procedure B as sticky solid in 66% yield (25.5 ng, 3f:4f=97:03); Reaction time 8 hours/35° C.; $R_f$ 0.5 (ethyl acetate:pet. ether, 1:4); $^1$H NMR (400 MHz, $CDCl_3$) δ (ppm) 7.37-7.32 (m, 1H), 7.27-7.22 (m, 1H), 7.12-7.07 (m, 1H), 7.06-7.00 (m, 1H), 4.12 (q, J=7.19 Hz, 2H), 3.79 (s, 2H), 3.77-3.68 (m, 1H), 3.52 (s, 2H), 1.77-1.63 (m, 4H), 1.50-1.34 (m, 3H), 1.23 (t, J=7.13 Hz, 3H), 1.07-0.97 (m, 2H), 0.9

(d, J=6.50 Hz, 3H); HRMS (ESI-TOF) m/z $[M+H]^+$ calcd for $C_{22}H_{27}NO_4F$, 388.1919; found, 388.1921.

xiv. Ethyl (Z)-2-(4-(3,4-difluorobenzyl)-2-((4-methylcyclohexyl)imino)-5-oxo-2,5-dihydrofuran-3-yl) acetate (3g)

The title compound 3g was prepared according to the general procedure B as sticky solid in 63% yield (25.5 mg, 3g:4g=95:05); Reaction time 8 hours/35° C.; $R_f$ 0.6 (ethyl acetate:pet. ether, 1:4); $^1$H NMR (400 MHz, $CDCl_3$) δ (ppm) 7.15-7.02 (m, 2H), 7.0-6.94 (m, 1H), 4.14 (q, J=7.25 Hz, 2H), 3.80-3.73 (m, 1H), 3.72 (s, 2H), 3.49 (s, 2H), 1.75-1.68 (m, 4H), 1.50-1.36 (m, 3H), 3.87 (t, J=7.25 Hz, 3H), 1.08-0.97 (m, 2H), 0.9 (d, J=6.1 Hz, 3H); HRMS (ESI-TOF) m/z $[M+H]^+$ calcd for $C_{22}H_{26}NO_4F_2$, 406.1824; found, 406.1829.

xv. Ethyl (Z)-2-(2-((4-methylcyclohexyl)imino)-5-oxo-4-(3-(trifluoro methyl) benzyl)-2,5-dihydrofuran-3-yl)acetate (3h)

The title compound 3h was prepared according to the general procedure B as sticky solid in 58% yield (25.3 mg, 3h:4h=98:02); Reaction time 8 hours/35° C.; $R_f$ 0.5 (ethyl acetate:pet. ether, 1:4); $^1$H NMR (400 MHz, $CDCl_3$) δ (ppm) 7.52 (d, J=6.88 Hz, 1H), 7.49 (s, 1H), 7.48-7.40 (m, 2H), 4.12 (q, J=7.13 Hz, 2H), 3.83 (s, 2H), 3.79-3.71 (m, 1H1), 3.487 (s, 2H), 1.76-1.69 (m, 4H), 1.50-1.34 (m, 3H), 1.22 (t, J=7.13 Hz, 3H), 1.09-0.98 (m, 2H), 0.90 (d, J=6.50 Hz, 3H); HRMS (ESI-TOF) m/Z $[M+H]^+$ calcd for $C_{23}H_{27}F_3NO$, 438.1887; found, 438.1892.

xvi. Ethyl (Z)-2-(2-((4-methylcyclohexyl)imino)-4-(4-nitrobenzyl)-5-oxo-2,5-dihydro furan-3-yl)acetate (3i)

The title compound 3i was prepared according to the general procedure B as sticky solid in 63% yield (26 mg, 3i:4i=96:04); Reaction time 8 hours/35° C.; $R_f$ 0.5 (ethyl acetate:pet. ether, 1:4); $^1$H NMR (400 MHz, $CDCl_3$) δ (ppm) 8.18 (d, 3=8.63 Hz, 2H), 7.44 (d, J=8.63 Hz, 2H), 4.14 (q, J=7.13 Hz, 2H), 3.87 (s, 2H), 3.80-3.70 (m, 1H), 3.53 (s, 2H), 1.78-1.67 (m, 4H), 1.47-1.35 (m, 3H), 1.24 (t, J=7.13 Hz, 3H), 1.09-0.99 (m, 2H), 0.9 (d, J=6.50 Hz, 3H); HRMS (ESI-TOF) in/z $[M+H]^+$ calcd for $C_{22}H_{27}N_2O_6$, 415.1864; found, 415.1867.

xvii. Ethyl (Z)-2-(2-((4-methylcyclohexyl)imino)-4-(naphthalen-2-yl methyl)-5-oxo-2,5-dihydrofuran-3-yl)acetate (3j)

The title compound 3j was prepared according to the general procedure B as sticky solid in 56% yield (23.4 mg, 3j:4j=99:01); Reaction time 8 hours/35° C.; $R_f$ 0.6 (ethyl acetate:pet. ether, 1:4); $^1$H NMR (400 MHz, $CDCl_3$) δ (ppm) 7.83-7.75 (m, 3H), 7.68 (s, 1H) 7.51-7.43 (m, 2H), 7.35 (d, J=8.38 Hz, 1H), 4.04 (q, J=7.13 Hz, 2H), 3.94 (s, 2H), 3.80-3.72 (m, 1H), 3.47 (s, 2H), 1.78-1.68 (m, 4H), 1.50-1.36 (m, 3-H), 1.15 (1, J=7.13 Hz, 3H), 1.08-0.98 (m, 2H), 0.9 (d, J=6.50 Hz, 3H); HRMS (ESI-TOF) m/z $[M+H]^+$ calcd for $C_{26}H_{30}NO_4$, 420.2169; found, 420.2177.

xviii. Ethyl (Z)-2-(4-(anthracen-9-ylmethyl)-2-((4-methylcyclohexyl)imino)-5-oxo-2,5-dihydrofuran-3-yl)acetate (3k)

The title compound 3k was prepared according to the general procedure B as sticky solid in 52% yield (24.3 mg, 3k:4k=98:02); Reaction time 8 hours/35° C.; $R_f$ 0.6 (ethyl acetate:pet. ether, 1:4); $^1$H NMR (400 MHz, $CDCl_3$) δ (ppm) 8.48 (s, 1H), 8.11-8.01 (m, 4H), 7.56-7.45 (m, 4H), 4.78 (s, 2H), 3.80-3.70 (m, 1H), 3.44 (q, J=7.25 Hz, 2H), 2.43 (s, 2H), 1.71-1.63 (m, 4H), 136-1.28 (m, 4H), 1.06-0.99 (m, 2H), 0.89-0.86 (m, 5H); HRMS (ESI-TOF) m/z $[M+H]^+$ calcd for $C_{30}H_{32}NO_4$, 470.2326; found, 470.2330.

xix. Ethyl (Z)-2-(2-((4-methylcyclohexyl)imino)-5-oxo-4-(pyridin-3-yl methyl)-2,5-dihydrofuran-3-yl) acetate (3h)

The title compound 3(1) was prepared according to the general procedure B as sticky solid in 53% yield (20 mg, 3l:4l=96:04); Reaction time 8 hours/35° C.; $R_f$0.4 (ethyl acetate:pet. ether, 1:2); $^1$H NMR (400 MHz, $CDCl_3$) δ (ppm) 8.57 (m, 2H), 7.64-7.55 (m, 1H), 7.26-7.22 (m, 1H), 4.13 (q, J=7.13 Hz, 2H), 3.77 (s, 2H), 7.76-3.70 (m, 1H), 3.51 (s, 2H), 1.75-1.67 (m, 4H), 1.49-1.34 (m, 3H), 1.23 (t, J=7.25 Hz, 3H), 1.08-0.97 (m, 2H), 0.90 (d, J=6.63 Hz, 3H); HRMS (ESI-TOF) m/z $[M+H]^+$ calcd for $C_{21}H_{27}N_2O_4$ 471.1970; found, 471.1966.

xx. Ethyl (Z)-2-(4-butyl-2-((4-methylcyclohexyl) imino)-5-oxo-2,5-dihydrofuran-3-yl)acetate (3m)

The title compound 3m was prepared according to the general procedure B as sticky solid in 72% yield (26 mg, 3m:4m=98:02); Reaction time 8 hours/35° C.; $R_f$ 0.6 (ethyl acetate:pet. ether, 1:4); $^1$H NMR (400 MHz, $CDCl_3$) δ (ppm) 4.16 (q, J=7.13 Hz, 2H), 3.8-3.7 (m, 1H), 3.51 (s, 2H), 2.39 (t, J=7.69 Hz, 2H), 1.77-166 (m, 4H), 1.58-1.50 (m, 2H), 1.46-1.32 (m, 5H), 1.26 (t, J=7.13 Hz, 3H), 1.10-0.98 (m, 2H), 0.95-0.87 (m, 6H); HRMS (ESI-TOF) m/z $[M+H]^+$ calcd for $C_{19}H_{30}NO_4$, 336.2169; found, 336.2174.

xxi. Ethyl (Z)-2-(2-((4-methylcyclohexyl)iminio)-4-nonyl-5-oxo-2,5-dihydrofuran-3-yl)acetate (3n)

The title compound 3n was prepared according to the general procedure B as sticky solid in 62% yield (25 mg, 3n:4n:=98:02); Reaction time 8 hours/35° C.; $R_f$ 0.7 (ethyl acetate:pet. ether, 1:4); $^1$H NMR (400 MHz, $CDCl_3$) δ (ppm) 4.16 (q, J=7.13 Hz, 2H), 3.39-3.67 (m, 1H), 3.51 (s, 2H), 2.39 (t, J=7.75 Hz, 2H), 1.78-1.69 (m, 4H), 1.60-1.52 (m, 2H), 1.48-1.40 (m, 2H), 1.33-1.22 (m, 18H), 1.09-0.98 (m, 2H), 0.9-0.88 (m, 6H); HRMS (ESI-TOF) m/z $[M+H]^+$ calcd for $C_{24}H_{40}NO_4$, 406.2952; found, 406.2954.

xxii. Ethyl (Z)-2-(4-(cyclohexylmethyl)-2-((4-methylcyclohexyl)imino)-5-oxo-2,5-dihydrofuran-3-yl) acetate (3o)

The title compound 3o was prepared according to the general procedure B as sticky solid in 63% yield (24 mg, 3o:4o=96:04); Reaction time 8 hours/35° C.; $R_f$ 0.7 (ethyl acetate:pet. ether, 1:4); $^1$H NMR (400 MHz, $CDCl_3$) δ (ppm) 4.16 (q, J=6.87 Hz, 2H), 3.79-3.67 (m, 1H), 3.50 (s, 2H), 2.29 (d, J=6.87 Hz, 2H), 1.81-1.57 (m, 12H), 1.50-1.35 (m, 3H), 1.26-1.23 (m, 4H), 1.21-1.15 (m, 2H), 1.05-0.97 (m, 2H), 0.91 (d, J=6.10 Hz, 3H); HRMS (ESI-TOF) m/z $[M+H]^+$ calcd for $C_{22}H_{34}NO_4$, 376.2482; found, 376.2487.

xxiii. Ethyl (Z)-2-(4-benzhydryl-2-((4-methylcyclohexyl)imino)-5-oxo-2,5-dihydrofuran-3-yl)acetate (3p)

The title compound 3p was prepared according to the general procedure B as sticky solid in 56% yield (25 mg, 3p:4p=96:04); Reaction time 8 hours/35° C.; $R_f$ 0.5 (ethyl acetate:pet. ether, 1:4); $^1$H NMR (400 MHz, $CDCl_3$) δ (ppm) 735-7.28 (m, 61H), 7.20 (d, J=7.25 Hz, 4H), 5.48 (s, 1H), 4.03 (q, J=7.25 Hz, 2H), 3.80-3.70 (m, 1H), 3.09 (s, 2H), 1.77-1.67 (m, 4H), 1.47-1.37 (m, 3H), 1.20 (t, J=7.06 Hz, 3H), 1.08-0.98 (m, 2H), 0.9 (d, J=6.49 Hz, 3H); HRMS (ESI-TOF) m/z $[M+H]^+$ calcd for $C_{28}H_{32}NO_4$, 446.2331; found, 446.2329.

xxiv. Ethyl (Z)-2-(4-benzyl-2-(hexylimino)-5-oxo-2,5-dihydrofuran-3-yl) acetate (3q)

The title compound 3q was prepared according to the general procedure B as sticky solid in 49% yield (17.4 mg, 3q:4q=96:04); Reaction time 8 hours/35° C., $R_f$ 0.5 (ethyl acetate:pet. ether, 1:4); $^1$H NMR (400 MHz, $CDCl_3$) δ (ppm) 7.37-7.27 (m, 2H), 7.27-7.17 (m, 3H), 4.12 (q, 1=7.63, 2H), 3.78 (s, 2H), 3.57 (J 7.63 Hz, 2H), 3.44 (s, 2H), 1.65-1.52 (m, 2H), 1.32-1.27 (m, 6H), 1.22 (t, J=6.87 Hz, 3H), 0.88 (t, J=6.87 Hz, 3H); HRMS (ESI-TOF) m/z $[M+H]^+$ calcd for $C_{21}H_{28}NO_4$, 358.2018; found, 358.2023.

xxv. Diethyl 2,2'-((2Z,2'Z)-(hexane-1,6-diylbis (azaneylylidene))bis(4-benzyl-5-oxo-2,5-dihydro-furan-3-yl-2-ylidene))diacetate (3r)

The title compound 3s was prepared according to the general procedure B as sticky solid in 48% yield (30 ng, 3s:4s=92:08); Reaction time 8 hours/35° C.; $R_f$ 0.3 (ethyl acetate:pet. ether, 1:4); $^1$H NMR (400 MHz, $CDCl_3$) δ (ppm) 7.33-7.30 (m, 4H), 7.28-7.22 (in 6H), 4.13 (q, J=6.87 Hz, 4H), 3.80 (s, 4H), 3.61-3.46 (m, 4H), 3.45 (s, 4H), 1.65-1.59 (m, 4H), 1.29-1.27 (m, 4H), 1.24 (q, J=7.25 Hz, 6); HRMS (ESI-TOF) m/z $[M+H]^+$ calcd for $C_{36}H_{41}N_2O_8$, 629.2862; found, 629.2863.

xxvi. Ethyl 2-(1,4-dibenzyl-2,5-dioxo-2,5-dihydro-1H-pyrrol-3-yl)acetate (4t)

The title compound 4t was prepared according to the general procedure C as sticky solid in 61% yield (22 mg, 3t:4t=75:25); Reaction time 8 hours/35° C.; $R_f$ 0.4 (ethyl acetate:pet. ether, 1:4); $^1$H NMR (500 MHz, $CDCl_3$) δ (ppm) 7.36-7.27 (m, 6H), 7.26-7.28 (m, 4H), 4.66 (s, 2H), 4.09 (q, J=7.25 Hz, 2H), 3.78 (s, 2H), 3.30 (s, 2H), 1.20 (t, J=7.25 Hz, 3H); HRMS (ESI-TOF) m/z $[M+H]^+$ calcd for $C_{22}H_{22}NO_4$, 364.1548. found, 364.1542.

xxvii. Ethyl 2-(4-benzyl-2,5-dioxo-1-phenyl-2,5-dihydro-1H-pyrrol-3-yl) acetate (4u)

The title compound 4u was prepared according to the general procedure C as white solid in 65% yield (22.6 mg, 3u:4u=15:85); Reaction time 8 hours/35° C.; $R_f$ 0.5 (ethyl acetate:pet. ether, 1:4); mp: 78-80° C.; $^1$H NMR (400 MHz, $CDCl_3$) of pure maleimide 4u δ (ppm) 7.46-739 (m, 2H), 7.39-7.28 (m, 5H), 7.28-7.21 (m, 3H), 4.13 (q, J=7.25 Hz, 2H), 3.86 (s, 2H), 3.40 (s, 2H), 1.23 (t, J=7.23 Hz, 3H); FIRMS (ESI-TOF) m/z: $[M+H]^+$ calcd for $C_{21}H_{20}NO_4$, 350.1392; found, 350.1397.

xxviii. Ethyl 2-(4-benzyl-2,5-dioxo-1-(p-tolyl)-2,5-dihydro-1H-pyrrol-3-yl) acetate (4v)

The title compound 4v was prepared according to the general procedure C as white solid in 59% yield (21 mg, 3v:4v=26:74); Reaction time 8 hours/35° C.; $R_f$0.5 (ethyl acetate:pet. ether, 1:4); mp: 85-87° C.; $^1$H NMR (400 MHz, $CDCl_3$) of pure maleimide 4v δ (ppm) 7.5-7.1 (m, 9H), 4.15 (q, 1=7.25 Hz, 2H), 3.88 (s, 2H), 3.41 (s, 2H), 2.38 (s, 3H), 1.25 (t, J=7.25 Hz, 3H); HRMS (ESI-TOF) m/z: $[M+H]^+$ calcd for $C_{22}H_{22}NO_4$, 364.1549; found, 364.1549.

xxix. Ethyl (Z)-2-(4-benzyl-2-((4-methoxyphenyl) imino)-5-oxo-2,5-dihydrofuran-3-yl)acetate (3w)

The title compound 3w was prepared according to the general procedure B and 3w was isolated as white solid in 23% yield separated from reaction mixture without refluxing in AcOH (8.7 mg, 3w:4w=33:67); Reaction time 8 hours/35° C.; $R_f$0.6 (ethyl acetate:pet, ether, 1:4); mp: 116-118° C.: $^1$H NMR (400 MHz, $CDCl_3$) of pure isomaleimide 3w δ (ppm) 7.47 (dd, J=9.13, 2.25 Hz, 2H), 7.34-7.28 (m, 2H), 7.27-7.22 (m, 3H), 6.88 (dd, J=9.13, 2.25 Hz, 2H), 4.14 (q, 1=7.13 Hz, 2H), 382 (s, 5H), 3.56 (2H), 1.23 (t, J=7.13, 3H); HRMS (ESI-TOF) m/z: $[M+H]^+$ calcd for $C_{22}H_{12}NO_5$, 380.1497; found, 380.1490.

xxx. Ethyl 2-(4-benzyl-1-(4-methoxyphenyl)-2,5-dioxo-2,5-dihydro-1H-pyrrol-3-yl)acetate (4w)

The title compound 4w was prepared according to the general procedure B as white solid in 45% yield, separated from reaction mixture without refluxing in AcOH (17 mg, 3w:4w=33:67); Reaction time 8 hours/35° C.; $R_f$ 0.4 (ethyl acetate:pet. ether, 1:4); mp: 129-131° C.; $^1$H NMR (400 MHz, $CDCl_3$) of pure maleimide 4w δ (ppm) 7.36-7.30 (m, 2H), 7.30-7.22 (m, 5H), 6.97 (d, J=6.97 Hz, 2H), 4.15 (q, J=7.25 Hz, 2H), 3.87 (s, 2H), 3.83 (s, 3H), 3.41 (s, 2H), 1.25 (t, J=7.25 Hz, 3H); HRMS (ESI-TOF) m/z: $[M+H]^+$ calcd for $C_{22}H_{22}NO_5$, 380.1497; found, 380.1497.

xxxi. Ethyl 2-(4-benzyl-1-(3-fluorophenyl)-2,5-dioxo-2,5-dihydro-1H-pyrrol-3-yl)acetate (4x) The title compound 4x The title compound 4x was prepared according to the general procedure C as white solid in 60% yield (22 ng, 3x:4x=24:76); Reaction time 8 hours/35° C.; $R_f$ 0.4 (ethyl acetate:pet. ether, 1:4); mp: 75-77° C.; $^1$H NMR (400 MHz, $CDCl_3$) of pure maleimide 4x δ (ppm) 7.44-7.37 (m, 1H), 7.35-7.30 (m, 2H), 7.30-7.22 (m, 4H), 7.22-7.17 (m, 1H), 7.07-7.02 (m, 1H), 4.15 (q, J=7.15 Hz, 2H), 3.88 (s, 2H), 3.42 (s, 2H), 1.25 (t, J=7.13 Hz, 3H); HRMS (ESI-TOF) m/z: $[M+H]^+$ calcd for $C_{22}H_{19}FNO_4$, 368.1298; found, 368.1306.

xxxii. Ethyl 2-(4-benzyl-1-(4-chlorophenyl)-2,5-dioxo-2,5-dihydro-1H-pyrrol-3-yl) acetate (4y)

The title compound 4y was prepared according to the general procedure C as pale yellow solid in 66% yield (25 mg, 3y:4y=14:86); Reaction time 8 hours/35° C.; $R_f$ 0.4 (ethyl acetate:pet. ether, 1:4) mp: 72-74° C.; $^1$H NMR (400 MHz, $CDCl_3$) of pure maleimide 4y δ (ppm) 7.45-7.39 (m, 2H), 7.37-7.34 (m, 2H), 7.34-7.23 (m, 5H), 4.16 (q, J=7.25 Hz, 2H), 3.88 (s, 2H), 3.42 (s, 2H), 1.25 (t, J=7.25 Hz, 3H); HRMS (ESI-TOF) m/z: $[M+H]^+$ calcd for $C_{21}H_{19}ClNO_4$, 384.1002; found, 384.0998.

xxxiii. Ethyl 2-(4-benzyl-1-(3,4-dichlorophenyl)-2,5-dioxo-2,5-dihydro-1H-pyrrol-3-yl) acetate (4z)

The title compound 4z was prepared according to the general procedure C as sticky solid in 70% yield (29 mg, 3z:4z=8:92); Reaction time 8 hours/35° C.; R-0.5 (ethyl acetate:pet. ether, 1:4); $^{1}$H NMR (400 MHz, $CDCl_3$) of pure maleimide 4z δ (ppm) 7.59 (d, J=2.38 Hz, 1H), 7.52 (d, J=8.63 Hz, 1H), 7.35-7.30 (ma, 3H), 7.30-7.24 (m, 3H), 4.16 (q, J=7.13 Hz, 2H), 3.87 (s, 2H), 3.42 (s, 2H), 1.26 (t, J=7.13 Hz, 3H); HRMS (ESI-TOF) m/z: $[M+H]^+$ calcd for $C_{21}H_{19}Cl_2NO_4$, 418.0612; found, 418.0620.

xxxiv. Ethyl 2-(4-benzyl-1-(4-chloro-3-nitrophenyl)-2,5-dioxo-2,5-dihydro-1H-pyrrol-3-yl)acetate (4aa)

The title compound 4aa was prepared according to the general procedure C as pale yellow solid in 59% yield (25 mg, 3aa:4aa=09:91); Reaction time 8 hours/35° C.; $R_f$ 0.4 (ethyl acetate:pet. ether, 1:4); mp: 79-81° C.; $^{1}$H NMR (400 MHz, $CDCl_3$) of pure maleimide 4aa δ (ppm) 8.12 (d, J=2.38 Hz, i H), 7.72 (dd, I=2.38, 8.76 Hz, 1H), 7.62 (d, J=8.76 Hz, 1H), 7.37-7.31 (m, 2H), 7.321-7.24 (m, 3H), 4.17 (q, J=7.25 Hz, 2H), 3.89 (s, 2H), 3.44 (s, 2H), 1.27 (t, J=7.13 Hz, 3H); HRMS (ESI-TOF) m/z:$[M+H]^+$ calcd for $C_{21}H_{18}ClN_2O_6$, 429.0853; found, 429.0857.

xxxv. Ethyl 2-(4-benzyl-1-(4-nitrophenyl)-2,5-dioxo-2,5-dihydro-H-pyrrol-3-yl) acetate (4ab)

The title compound 4ab was prepared according to the general procedure C as pale yellow solid in 68% yield (27 mg, 3ab:4ab=11:89); Reaction time 8 hours/35° C.; $R_f$ 0.4 (ethyl acetate:pet. ether, 1:4); mp: 95-97° C.; $^{1}$H NMR (400 MHz, $CDCl_3$) of pure maleimide 4ab δ (ppm) 8.31 (dd, J=9.2, 2.13 Hz, 2H), 7.72 (dd, J=9.2, 2.13 Hz, 2H), 7.37-7.31 (m, 2H), 7.30-7.23 (m, 3H), 4.17 (q, J=7.13 Hz, 2H), 3.90 (s, 2H), 3.45 (s, 2H), 1.27 (t, J=7.13 Hz, 3H); HRMS (ESI-TOF) m/z:$[M+H]^+$ calcd for $C_{21}H_{19}N_2O_6$, 395.1243; found, 395.1235.

xxxvi. Ethyl 2-(4-(2,5-dimethoxybenzyl)-1-(4-nitrophenyl)-2,5-dioxo-2,5-dihydro-1H-pyrrol-3-yl)acetate (4ac)

The title compound 4ac was prepared according to the general procedure C as pale yellow solid in 65% yield (29.5 mg, 3ac:4ac=12:88); Reaction time 8 hours/35° C.; $R_f$ 0.3 (ethyl acetate:pet. ether, 1:4); mp: 93-95° C.; $^{1}$H NMR (400 MHz, $CDCl_3$) of pure maleimide 4ac δ (ppm) 8.31 (d, J=9.26 Hz, 2H), 7.72 (d, J=9.26 Hz, 2H), 6.94-6.90 (m, 1H), 6.80-6.77 (m, 2H), 4.17 (q, J=7.25 Hz, 2H), 3.83 (s, 2H), 3.79 (s, 3H), 3.77 (s, 3H), 3.53 (s, 2H), 1.27 (t, J=7.13 Hz, 3H); HRMS (ESI-TOF) m/z:$[M+H]^+$ calcd for $C_{23}H_{23}N_2O_8$, 455.1454; found, 455.1444.

xxxvii. Ethyl 2-(4-(4-chlorobenzyl)-1-(4-nitrophenyl)-2,5-dioxo-2,5-dihydro-1H-pyrrol-3-yl)acetate (4ad)

The title compound 4ad was prepared according to the general procedure C as sticky solid in 70% yield (30 mg, 3ad:4ad=09:91); Reaction time 8 hours/35° C.; $R_f$ 0.5 (ethyl acetate:pet. ether, 1:4); $^{1}$H NMR (400 MHz, $CDCl_3$) of pure maleimide 4ad δ (ppm) 8.32 (dd, J=7.17, 2.20 Hz, 2H), 7.71 (dd, J=7.17, 2.20 Hz, 2H), 7.35-7.27 (m, 2H), 7.26-7.18 (m, 2H), 4.18 (q, J=7.17 Hz, 2H), 3.87 (s, 2H), 3.48 (s, 2H), 1.28 (t, J=7.17 Hz, 3H); HRMS (ESI-TOF) m/z: $[M+H]^+$ calcd for $C_{21}H_{18}ClN_2O_6$, 429.0853; found, 429.0873.

xxxviii. Ethyl 2-(4-(4-nitrobenzyl)-1-(4-nitrophenyl)-2,5-dioxo-2,5-dihydro-1H-pyrrol-3-yl)acetate (4ae)

The title compound 4ae was prepared according to the general procedure C as yellow solid in 58% yield (25.5 mg, 3ae:4ae=4ae>99); Reaction time 8 hours/35° C.; $R_f$ 0.4 (ethyl acetate:pet. ether, 1:4); mp: 104-106° C.; $^{1}$H NMR (400 MHz, $CDCl_3$) of pure maleimide 4ae δ (ppm) 8.31 (d, J=9.16 Hz, 2H), 8.19 (d, J=8.39 Hz, 2H), 7.70 (d, J=9.16 Hz, 2H), 7.49 (d, J=8.39 Hz, 2H), 4.20 (d, J=7.25 Hz, 2H), 4.0 (s, 2H), 3.55 (s, 2H), 1.28 (t, J=7.63 Hz, 3H HRMS (ESI-TOF) m/z: $[M+H]^+$ calcd for $C_{21}H_{18}N_3O_8$, 440.1093; found, 440.1097.

xxxix. Ethyl 2-(4-(naphthalen-2-ylmethyl)-1-(4-nitrophenyl)-2,5-dioxo-2,5-dihydro-1H-pyrrol-3-yl) acetate (4af)

The title compound 4af was prepared according to the general procedure C as pale yellow solid in 53% yield (23.5 mg, 3af:4af=4af>99); Reaction time 8 hours/35° C.; $R_f$ 0.4 (ethyl acetate:pet. ether, 1:4); mp:112-114° C.; $^{1}$H NMR (400 MHz, $CDCl_3$) of pure maleimide 4af δ (ppm) 8.31 (dd, J=9.26, 2.13 Hz, 2H), 7.85-7.77 (m, 3H), 7.76-7.70 (m, 3H), 7.52-7.46 (m, 2H), 7.40-7.35 (m, 11H), 4.10 (q, J=7.13 Hz, 2H), 4.07 (s, 2H), 3.47 (s, 2H), 1.18 (t, J=7.25 Hz, 3H); HRMS (ESI-TOF) m/z: $[M+H]^+$ calcd for $C_{25}H_{21}N_2O_6$, 444.1321; found, 444.1320.

xl. Ethyl 2-(1-(4-nitrophenyl)-4-nonyl-2,5-dioxo-2,5-dihydro-1H-pyrrol-3-yl) acetate (4ah)

The title compound 4ah was prepared according to the general procedure C as sticky solid in 47% yield (20 mg, 3ah:4ah=10:90); Reaction time 8 hours/35° C.; $R_f$ 0.5 (ethyl acetate:pet. ether, 1:4); $^{1}$H NMR (500 MHz, $CDCl_3$) of pure maleimide 4ah δ (ppm) 8.32 (d, J=9.16 Hz, 2H), 7.74 (d, J=9.16 Hz, 2H) 4.23 (q, J=6.87 Hz, 2H), 3.55 (s, 2H), 2.52 (t, J=7.63 Hz, 2H), 1.65-1.58 (m, 2H), 1.33-1.27 (m, 12H), 0.89 (t, J=6.48 Hz, 3H); ESI-Mass $(M+Na)^+$ 453.1.

xii. Ethyl (Z)-2-(4-(4-bromobenzyl)-5-oxo-2-(phenylimino)-2,5-dihydrofuran-3-yl) acetate (3ai)

The title compound 3ai was prepared according to the general procedure B as white solid in 17% yield, separated from reaction mixture without refluxing in AcOH (8 mg, 3ai:4ai=24:76); Reaction time 8 hours/35° C.; $R_f$ 0.6 (ethyl acetate:pet. ether, 1:4); mp: 80-82° C.; $^{1}$H NMR (400 MHz, $CDCl_3$) of pure isomaleimide 3ai δ (ppm) 7.47 (m, 2H), 7.41-7.33 (m, 4H), 7.25-7.21 (11H), 7.17-7.13 (m, 2H), 4.17 (q, J=7.13 Hz, 2H), 3.79 (s, 2H), 3.61 (s, 2H), 1.26 (J=7.25 Hz, 3H); HRMS (ESI-TOF) m/z: $[M+H]^+$ calcd for $C_2H_{19}BrNO_4$, 428.0497; found, 428.0493.

xlii. Ethyl 2-(4-(4-bromobenzyl)-2,5-dioxo-1-phenyl-2,5-dihydro-1H-pyrrol-3-yl) acetate (4ai)

The title compound 4ai was prepared according to the general procedure B as white solid in 49% yield, separated from reaction mixture without refluxing in AcOH (23 mg, 3ai:4ai=24:76); Reaction time 8 hours/35° C.; $R_f$ 0.5 (ethyl acetate:pet. ether, 1:4); mp:98-100° C.; $^{1}$H NMR (400 MHz, $CDCl_3$) of pure maleimide 4ai δ (ppm) 7.50-7.41 (m, 4H), 7.40-7.32 (m, 3H), 7.20-7.17 (m, 2H), 4.16 (q, J=7.13 Hz, 2H), 3.83 (s, 2H), 3.45 (s, 2H), 1.27 (t, J=7.13 Hz, 3H), HRMS (ESI-TOF) m/z: $[M+H]^+$ calcd for $C_{21}H_{19}BrNO_4$, 428.0497; found, 428.0498.

xliii. Ethyl 2-(4-benzyl-1-(4-methylcyclohexyl)-2,5-dioxo-2,5-dihydro-1H-pyrrol-3-yl) acetate (4a)

The title compound 4a was prepared according to the experimental procedure of step a3 (example 5) as sticky solid in 90% yield (18 mg) Reaction time 4 hours/120° C.; $R_f$ 0.6 (ethyl acetate:pet. ether, 1:4); $^1H$ NMR (400 MHz, $CDCl_3$) of pure maleimide 4ac δ (ppm) 7.34-7.27 (m, 2H), 7.27-7.17 (m, 3H), 4.11 (q, J=6.87 Hz, 2H), 3.92-3.82 (m, 1H), 3.76 (s, 2H), 3.28 (s, 2H), 2.15-2.03 (m, 2H), 1.76 (m, 2H), 1.64-1.62 (m, 2H), 1.46-1.37 (m, 1H), 1.22 (t, J=6.87 Hz, 3H), 1.07-0.95 (m, 2H), 0.9 (d, J=6.10 Hz, 3H); HRMS (ESI-TOF) m/z: $[M+H]^+$ calcd for $C_{22}H_{23}NO_4$, 370.2018; found, 370.2010.

xliv. Ethyl 2-(4-hexyl-2,5-dioxo-1-(p-tolyl)-2,5-dihydro-1H-pyrrol-3-yl)acetate (4aj)

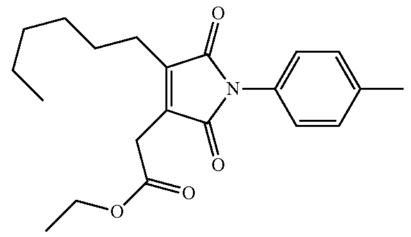 [SMILES: CCCCCCC1=C(CC(=O)OCC)C(=O)N(c2ccc(C)cc2)C1=O]

The title compound was prepared according to the general procedure of example 6 step 1 as yellow oil (the title compound was characterized as a pure maleimide by separating it from reaction mixture) (43 mg) Reaction time 8 hours/35° C.; $R_f$ 0.7 (ethyl acetate:pet. ether, 1:4); $^1H$ NMR (400 MHz, $CDCl_3$) δ (ppm) 7.27-7.20 (m, 4H), 4.21 (q, J=7.13 Hz, 2H), 3.52 (s, 3H), 2.49 (t, J=7.88 Hz, 2H), 2.38 (s, 3H), 1.62-1.57 (m, 2H), 1.37-1.26 (m, 9H), 0.90 (t, J=7.0 Hz, 3H); ESI-Mass $(M+H)^+$ 358.1.

xlv. 2-(4-hexyl-2,5-dioxo-2,5-dihydrofuran-3-yl) acetic acid (*Aspergillus* FH-X-213)

The title compound was prepared according to the general procedure of example 6 step 2 starting from the mixture of compound obtained by procedure of example 6, step 1 as thick oil in 45% yield (over two steps, 22 mg); $R_f$ 0.4 (ethyl acetate:pet. ether, 1:1): $^1H$ NMR (400 MHz, $CDCl_3$) δ (ppm) 3.57 (s, 2H), 2.50 (t, J=7.88 Hz, 2H), 1.61 (quintet, J=7.75 Hz, 2H), 1.36-1.28 (m, 6H), 0.89 (t, J=6.88 Hz, 3); HEMS (EST-TOF) m/z: $[M+H]^+$ calcd for $C_{12}H_{17}O_5$, 241.1075; found, 241.1088.

Example 8

The compounds were evaluated for anti-cancer activity by testing them against breast cancer cell lines obtained from NCCS, Pune, India. The MITT assay was carried out. The assay procedure involves reconstitution of the pre-measured MTT reagent in the assay buffer, followed by its addition to the culture system. After dissolving the formazan crystals in the solubilization solution, results can be directly read on a suitable reader.

Protocol

1. Harvest the cells;
2. Seed 10,000 cells in 100 μl DMEM media/well in 96-well microtiter plate in triplicate;
3. Incubate the cells at 37° C., 5% $CO_2$ for 24 hours to achieve morphology;
4. Treat the cells with varying concentrations of drugs;
5. Controls included untreated cells and cells treated with 100 uM Doxorubicin;
6. Incubate the cells for 72 hours after treatment;
7. Add 10 μl of MTT to each well, including controls;
8. Wrap the plate with aluminium foil to avoid exposure to light;
9. Return the plate to the incubator for 2 hours;
10. Observe the cells under an inverted microscope for presence of intracellular needle-shaped, dark purple coloured precipitate;
11. When the purple precipitate is clearly visible under the microscope, add 100 μl of solubilization solution to the wells;
12. Stir gently on a gyratory shaker to enhance dissolution of the crystals;
13. Read the absorbance on a spectrophotometer or an ELISA reader at 570 nm with a reference wavelength higher than 650 nm.

ADVANTAGES OF INVENTION

The present invention provides NHC-catalyzed highly selective enolate-driven intermolecular annulation of α,β-unsaturated aldehydes with carbamoyl alkylates leading to the substrate specific, scalable and general synthesis of synthetically valuable products of Formula (I).

The choice of carbamoyl alkylates as an optimal electrophilic reacting substrate is critical in the present NHC-catalyzed reactions to achieve the enolate pathway-based procedure to form the highly functionalized maleimides and isomaleimides as depicted in FIG. 1.

The conversion via NHC-enolate pathway has (i) Good functional group tolerance, (ii) has substrate dependent high selectivity and (iii) the process is carried out under mild reaction condition.

We claim:

1. A functionalized maleimide and isomaleimide of Formula (I):

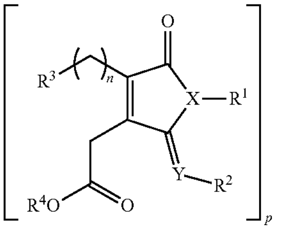

(I)

wherein, X and Y independently of each other represent heteroatom selected from nitrogen or oxygen;

$R^1$, $R^2$, and $R^3$ independently of each other represent unsubstituted or substituted alkyl, unsubstituted or substituted cycloalkyl, unsubstituted or substituted carbocycle, unsubstituted or substituted benzyl, unsubstituted or substituted aryl or unsubstituted or substituted heterocyclyl;

$R^4$ independently of each other represent hydrogen or $C_{1-4}$ alkyl,

'n' is the integer 1 to 9;

'p' is the integer 1to 2 with the proviso, when 'X' is oxygen, 'Y' is nitrogen and $R^1$ is absent;

when 'Y' is oxygen, 'X' is nitrogen and $R^2$ is absent;

when 'p' is 2, the compound is a bisimide or its congeners at $R^2$;

excluding the compounds wherein,

'X', 'Y', are oxygen, $R^1$ and $R^2$ are absent, $R^3$ is methyl, 'm' is the integer 1, 'n' is the integer 5 and $R^4$ is hydrogen;

'X' is nitrogen, 'Y is oxygen, $R^1$ is p-tolyl, $R^3$ is methyl, 'm' is the integer 1, 'n' is the integer 5 and $R^4$ is ethyl.

2. The functionalized maleimide and isomaleimide of Formula (I) as claimed in claim 1, wherein the maleimide and isomaleimide are selected from Ethyl (Z)-2-(4-benzyl-2-((4-methylcyclohexyl) imino)-5-oxo-2,5-dihydrofuran-3-yl) acetate (3a) and its maleimide isomer (4a); Ethyl (Z)-2-(4-(3-methylbenzyl)-2-((4-methylcyclohexyl) imino)-5-oxo-2,5-dihydrofuran-3-yl) acetate (3b) and its maleimide isomer (4b); Ethyl (Z)-2-(2-((4-methylcyclohexyl) imino)-5-oxo-4-(3-phenoxybenzyl)-2,5-dihydrofuran-3-yl) acetate (3c) and its maleimide isomer (4c); Ethyl (Z)-2-(4-(2,5-dimethoxy benzyl)-2-((4-methylcyclohexyl) imino)-5-oxo-2,5-dihydrofuran-3-yl) acetate (3d) and its maleimide isomer (4d); Ethyl (Z)-2-(4-(4-chlorobenzyl)-2-((4-methylcyclohexyl) imino)-5-oxo-2,5-dihydrofuran-3-yl) acetate (3e) and its maleimide isomer (4e); Ethyl (Z)-2-(4-(2-fluorobenzyl)-2-((4-methylcyclohexyl) imino)-5-oxo-2,5-dihydrofuran-3-yl) acetate (3f) and its maleimide isomer (4f); Ethyl (Z)-2-(4-(3,4-difluorobenzyl)-2-((4-methyl cyclohexyl) imino)-5-oxo-2,5-dihydrofuran-3-yl) acetate (3g) and its maleimide isomer (4g); Ethyl (Z)-2-(2-((4-methylcyclohexyl) imino)-5-oxo-4-(3-(trifluoromethyl) benzyl)-2,5-dihydrofuran-3-yl) acetate (3h) and its maleimide isomer (4h); Ethyl (Z)-2-(2-((4-methyl cyclohexyl) imino)-4-(4-nitrobenzyl)-5-oxo-2,5-dihydrofuran-3-yl) acetate (3i) and its maleimide isomer (4i); Ethyl (Z)-2-(2-((4-methylcyclohexyl) imino)-4-(naphthalen-2-ylmethyl)-5-oxo-2,5-dihydrofuran-3-yl) acetate (3j) and its maleimide isomer (4j); Ethyl (Z)-2-(4-(anthracen-9-ylmethyl)-2-((4-methyl cyclohexyl) imino)-5-oxo-2,5-dihydrofuran-3-yl) acetate (3k) and its isomer maleimide (4k); Ethyl (Z)-2-(2-((4-methylcyclohexyl) imino)-5-oxo-4-(pyridin-3-ylmethyl)-2,5-dihydrofuran-3-yl) acetate (31) and its maleimide isomer (41); Ethyl (Z)-2-(4-butyl-2-((4-methylcyclohexyl) imino)-5-oxo-2,5-dihydrofuran-3-yl) acetate (3m) and its maleimide isomer (4m); Ethyl (Z)-2-(2-((4-methylcyclohexyl) imino)-4-nonyl-5-oxo-2,5-dihydrofuran-3-yl) acetate (3n) and its maleimide isomer (4n); Ethyl (Z)-2-(4-(cyclohexylmethyl)-2-((4-methylcyclohexyl) imino)-5-oxo-2,5-dihydrofuran-3-yl) acetate (30) and its maleimide isomer (40); Ethyl (Z)-2-(4-benzhydryl-2-((4-methylcyclohexyl) imino)-5-oxo-2,5-dihydrofuran-3-yl) acetate (3p) and its maleimide isomer (4p); Ethyl (Z)-2-(4-benzyl-2-(hexylimino)-5-oxo-2,5-dihydrofuran-3-yl) acetate (3q) and its maleimide isomer (4q); Diethyl 2,2'-((2Z,2'Z)-(hexane-1,6-diylbis (azaneylylidene)) bis(4-benzyl-5-oxo-2,5-dihydrofuran-3-yl-2-ylidene)) diacetate (3r) and its maleimide isomer (4r); Ethyl (Z)-2-(4-benzyl-2-((4-methoxyphenyl) imino)-5-oxo-2,5-dihydrofuran-3-yl) acetate (3s); Ethyl 2-(4-benzyl-1-(4-methylcyclohexyl)-2,5-dioxo-2,5-dihydro-1H-pyrrol-3-yl) acetate (4a); Ethyl 2-(1,4-dibenzyl-2,5-dioxo-2,5-dihydro-1H-pyrrol-3-yl) acetate (4t); Ethyl 2-(4-benzyl-2,5-dioxo-1-phenyl-2,5-dihydro-1H-pyrrol-3-yl) acetate (4u) and its isomaleimide isomer (3u); Ethyl 2-(4-benzyl-2,5-dioxo-1-(p-tolyl)-2,5-dihydro-1H-pyrrol-3-yl) acetate (4v) and its isomaleimide isomer (3v); Ethyl 2-(4-benzyl-1-(4-methoxyphenyl)-2,5-dioxo-2,5-dihydro-1H-pyrrol-3-yl) acetate (4w) and its isomaleimide isomer (3w); Ethyl 2-(4-benzyl-1-(3-fluorophenyl)-2,5-dioxo-2,5-dihydro-1H-pyrrol-3-yl) acetate (4x) and its isomaleimide isomer (3x); Ethyl 2-(4-benzyl-1-(4-chlorophenyl)-2,5-dioxo-2,5-dihydro-1H-pyrrol-3-yl) acetate (4y) and its isomaleimide isomer (3y); Ethyl 2-(4-benzyl-1-(3,4-dichlorophenyl)-2,5-dioxo-2,5-dihydro-1H-pyrrol-3-yl) acetate (4z) and its isomaleimide isomer (3z); Ethyl 2-(4-benzyl-1-(4-chloro-3-nitrophenyl)-2,5-dioxo-2,5-dihydro-1H-pyrrol-3-yl) acetate (4aa) and its isomaleimide isomer (3aa); Ethyl 2-(4-benzyl-1-(4-nitrophenyl)-2,5-dioxo-2,5-dihydro-1H-pyrrol-3-yl) acetate (4ab) and its isomaleimide isomer (3ab); Ethyl 2-(4-(2,5-dimethoxybenzyl)-1-(4-nitrophenyl)-2,5-dioxo-2,5-dihydro-1H-pyrrol-3-yl) acetate (4ac) and its isomaleimide isomer (3ac); Ethyl 2-(4-(4-chlorobenzyl)-1-(4-nitrophenyl)-2,5-dioxo-2,5-dihydro-1H-pyrrol-3-yl) acetate (4ad) and its isomaleimide isomer (3ad); Ethyl 2-(4-(4-nitrobenzyl)-1-(4-nitrophenyl)-2,5-dioxo-2,5-dihydro-1H-pyrrol-3-yl) acetate (4ae) and its isomaleimide isomer (3ae); Ethyl 2-(4-(naphthalen-2-ylmethyl)-1-(4-nitrophenyl)-2,5-dioxo-2,5-dihydro-1H-pyrrol-3-yl) acetate (4af) and its isomaleimide isomer (3af); Ethyl 2-(1-(4-nitrophenyl)-4-nonyl-2,5-dioxo-2,5-dihydro-1H-pyrrol-3-yl) acetate (4ah) and its isomaleimide isomer (3ah); Ethyl 2-(4-(4-bromobenzyl)-2,5-dioxo-1-phenyl-2,5-dihydro-1H-pyrrol-3-yl) acetate (4ai) and its isomaleimide isomer (3ai).

3. The functionalized maleimide and isomaleimide of Formula (I) as claimed in claim 1, wherein the functionalized maleimide and isomaleimide of Formula (I) are applicable as anti-cancer agents.

4. The functionalized maleimide and isomaleimide of Formula (I) as claimed in claim 3, wherein the functionalized maleimide and isomaleimide of Formula (I) exhibit equal to or more than 50% of cell death when tested against breast cancer cell lines.

5. A process for preparation of functionalized maleimide and isomaleimide of Formula (I), wherein the process comprises: reacting N-heterocyclic carbene (NHC)-catalyzed [3+2] annulation of α,β-unsaturated aldehydes of Formula (II), with carbamoyl alkylates of Formula (III) in presence of NHC precursors, a base, and a solvent to obtain compounds of Formula (I);

(I)

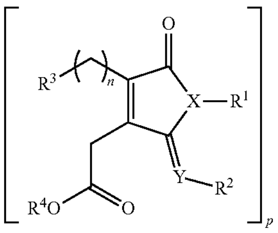

(II)

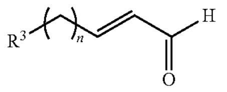

-continued (III)

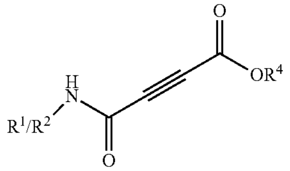

wherein $R^3$ in Formula (II) independently of each other represent the groups selected from unsubstituted or substituted alkyl, unsubstituted or substituted cycloalkyl, unsubstituted or substituted carbocycle, unsubstituted or substituted benzyl, unsubstituted or substituted aryl or unsubstituted or substituted heterocyclyl; and 'n' represents the integer 1 to 9;

wherein $R^1$ or $R^2$ in Formula (III) represent the groups selected from unsubstituted or substituted alkyl, unsubstituted or substituted cycloalkyl, unsubstituted or substituted carbocycle, unsubstituted or substituted benzyl, unsubstituted or substituted aryl or unsubstituted or substituted heterocyclyl; and $R^4$ in Formula (III) represents hydrogen or $C_{1-4}$ alkyl.

6. The process as claimed in claim 5, wherein the NHC precursors are selected from the group consisting of NHC-A, NHC-B, NHC-C, NHC-D, NHC-E, NHC-F, NHC-G, NHC-H, NHC-I, and NHC-J;

A

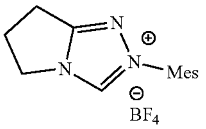

B

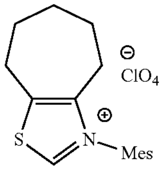

C

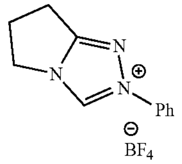

D

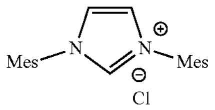

E

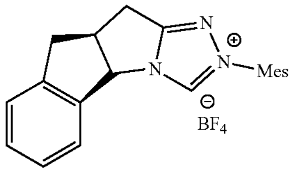

-continued

F

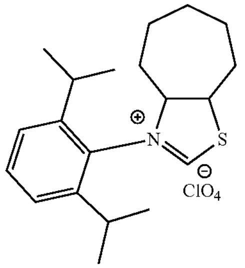

G

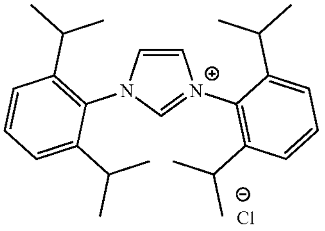

H

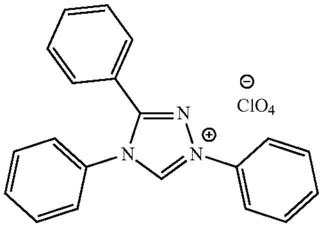

I

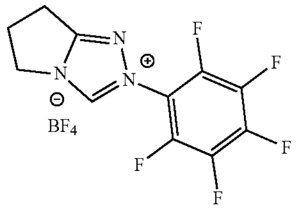

J

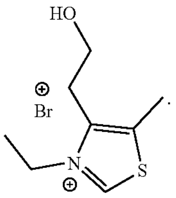

7. The process as claimed in claim 5, wherein the solvent is a polar or a non-polar solvent, a protic or an aprotic solvent, or an aliphatic or an aromatic solvent.

8. The process as claimed in claim 7, wherein the solvent is toluene.

9. The process as claimed in claim 5, wherein the base is selected from the group consisting of a carbonate and a bicarbonate of alkali and alkaline earth metals.

10. The process as claimed in claim 9, wherein the base is a carbonate of an alkali metal.

11. The process as claimed in claim 10, wherein the base is potassium carbonate.

12. The process as claimed in claim 5, wherein the reaction is carried out at a temperature in a range of 30-40° C. for a period of 8 hours.

13. The process as claimed in claim 5, wherein reacting N-heterocyclic carbene (NHC)-catalyzed [3+2] annulation of α,β-unsaturated aldehydes of Formula (II) with carbamoyl alkylates of Formula (III) comprises:

reacting trans-2-octenal (Formula (II)) with ethyl 4-oxo-4-(p-tolylamino) but-2-ynoate (2g) (Formula (III)) in presence of $K_2CO_3$ in toluene to obtain Ethyl 2-(4-hexyl-2,5-dioxo-1-(p-tolyl)-2,5-dihydro-1H-pyrrol-3-yl) acetate (4aj) and its isomer ethyl (Z)-2-(4-hexyl-5-oxo-2-(p-tolylimino)-2,5-dihydrofuran-3-yl) acetate (3aj); and evaporating toluene in vacuum and refluxing the residue in THF: methanol (1:2) and aq. KOH followed by purification to obtain a compound of Formula (I), wherein the compound of Formula (I) is *Aspergillus* FH-X-213;

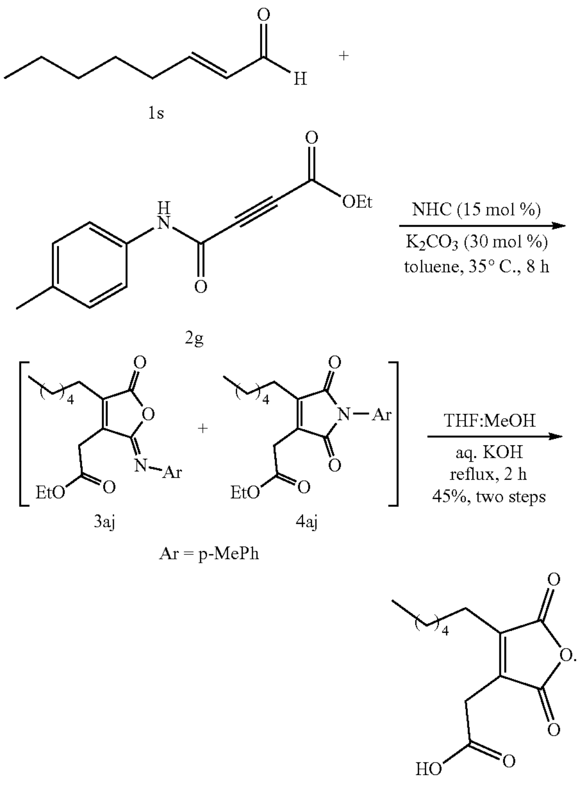

1s

2g

3aj

4aj

Ar = p-MePh

Aspergillus FH-X-213

14. The process as claimed in claim 13, wherein the reaction is carried out at a temperature in a range of 30-40° C.

15. A pharmaceutical composition containing functionalized maleimides and isomaleimides of Formula (I) together with at least one acceptable excipient.

16. The pharmaceutical composition as claimed as claimed in claim 15, wherein Formula (I) encompasses isomer compounds, isomaleimides of Formula (Ia) and maleimides of Formula (Ib) in varying proportions represented below, (Ia)

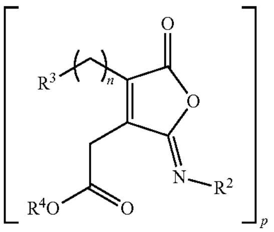

wherein $R^1$, $R^2$ and $R^3$ independently of each other represent unsubstituted or substituted alkyl, unsubstituted or substituted cycloalkyl, unsubstituted or substituted carbocycle, unsubstituted or substituted benzyl, unsubstituted or substituted aryl or unsubstituted or substituted heterocyclyl; $R^4$ represent hydrogen or $C_{1-4}$ alkyl;
'n' is the integer 1 to 9;
'p' is the integer 1,2
with the proviso,
when 'p' is 2, the compound is a bisimide or its congeners at $R^2$,
The compounds of Formula (Ib):

(Ib)

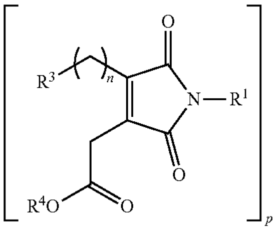

wherein $R^1$, $R^2$ and $R^3$ independently of each other represent unsubstituted or substituted alkyl, unsubstituted or substituted cycloalkyl, unsubstituted or substituted carbocycle, unsubstituted or substituted benzyl, unsubstituted or substituted aryl or unsubstituted or substituted heterocyclyl; $R^4$ represent hydrogen or $C_{1-4}$ alkyl;
'n' is the integer 1 to 9;
'p' is the integer 1,2
with the proviso,
when 'p' is 2, the compound is a bisimide or its congeners at $R^2$;
excluding the compound wherein,
'X' is nitrogen, 'Y is oxygen, $R^1$ is p-tolyl, $R^3$ is methyl 'n' is the integer 5 and $R^4$ is ethyl.

* * * * *